US009415083B2

(12) United States Patent
Massimino et al.

(10) Patent No.: US 9,415,083 B2
(45) Date of Patent: Aug. 16, 2016

(54) METHOD FOR DECREASING INFLAMMATION AND STRESS IN A MAMMAL

(75) Inventors: Stefan Patrick Massimino, Portland, OR (US); Gary Mitchell Davenport, Dayton, OH (US); Michael Griffin Hayek, Dayton, OH (US); George Roth, Pylesville, MD (US); Donald K. Ingram, Ellicott City, MD (US)

(73) Assignee: MARS, INCORPORATED, McLean, VA (US)

( * ) Notice: Subject to any disclaimer, the term of this patent is extended or adjusted under 35 U.S.C. 154(b) by 0 days.

(21) Appl. No.: 12/012,317

(22) Filed: Feb. 1, 2008

(65) Prior Publication Data

US 2008/0260866 A1    Oct. 23, 2008

Related U.S. Application Data

(63) Continuation-in-part of application No. 10/842,301, filed on May 10, 2004, now Pat. No. 7,666,459.

(60) Provisional application No. 60/898,788, filed on Feb. 1, 2007.

(51) Int. Cl.
*A61K 36/00*  (2006.01)
*A61K 36/54*  (2006.01)
*A61K 31/70*  (2006.01)

(52) U.S. Cl.
CPC ............... *A61K 36/54* (2013.01); *A61K 31/70* (2013.01)

(58) Field of Classification Search
None
See application file for complete search history.

(56) References Cited

U.S. PATENT DOCUMENTS

| | | | |
|---|---|---|---|
| 571,521 A | 11/1896 | Heberline et al. | |
| 1,086,936 A | 2/1914 | Pounder et al. | |
| 1,503,094 A | 7/1924 | Cramer | |
| 2,473,773 A | 6/1949 | West | |
| 2,540,979 A | 2/1951 | Clymer et al. | |
| 2,641,548 A | 6/1953 | Heinrich | |
| 3,320,130 A | 5/1967 | Henry | |
| 3,398,001 A | 8/1968 | Benson | |
| 3,429,426 A | 2/1969 | Wolf et al. | |
| 3,431,338 A | 3/1969 | Munzel | |
| 3,677,898 A | 7/1972 | Mitsugi | |
| 3,897,572 A | 7/1975 | Riggs et al. | |
| 3,898,132 A | 8/1975 | Heltrick | |
| 3,931,885 A | 1/1976 | Nahill et al. | |
| 3,957,974 A | 5/1976 | Hata | |
| 3,989,822 A | 11/1976 | Whistler | |
| 4,248,857 A | 2/1981 | DeNeale et al. | |
| 4,295,567 A | 10/1981 | Knudsen et al. | |
| 4,314,995 A | 2/1982 | Hata et al. | |
| 4,332,790 A | 6/1982 | Sozzi et al. | |
| 4,338,346 A | 7/1982 | Brand | |
| 4,399,163 A | 8/1983 | Brennan et al. | |
| 4,403,623 A | 9/1983 | Mark | |
| 4,411,925 A | 10/1983 | Brennan et al. | |
| 4,423,029 A | 12/1983 | Rizzi | |
| 4,434,231 A | 2/1984 | Jung | |
| 4,518,696 A | 5/1985 | Gehrman et al. | |
| 4,592,748 A | 6/1986 | Jost | |
| 4,647,453 A | 3/1987 | Meismer | |
| 4,736,849 A | 4/1988 | Leonard et al. | |
| 4,764,389 A | 8/1988 | LaBarge | |
| 4,767,623 A | 8/1988 | Conway et al. | |
| 4,781,939 A | 11/1988 | Martin et al. | |
| 4,786,507 A * | 11/1988 | Schmidt .................... 424/472 |
| 4,797,289 A | 1/1989 | Reddy | |
| 4,806,368 A | 2/1989 | Reddy | |
| 4,808,626 A | 2/1989 | Friedman | |
| 4,814,193 A | 3/1989 | Shenouda | |
| 4,816,259 A | 3/1989 | Matthews et al. | |
| 4,859,377 A | 8/1989 | Shasha et al. | |
| 4,889,238 A | 12/1989 | Batchelor | |
| 4,935,247 A | 6/1990 | Martila et al. | |
| 4,937,077 A | 6/1990 | Deetz, III | |
| 5,032,399 A | 7/1991 | Gorbach et al. | |
| 5,096,717 A | 3/1992 | Wirth et al. | |
| 5,132,137 A | 7/1992 | Reimann | |
| 5,160,745 A | 11/1992 | DeLuca et al. | |
| 5,171,580 A | 12/1992 | Imartino et al. | |
| 5,176,911 A | 1/1993 | Tosi et al. | |
| 5,286,495 A | 2/1994 | Batich et al. | |
| 5,292,657 A | 3/1994 | Rutherford | |
| 5,296,233 A | 3/1994 | Batista et al. | |

(Continued)

FOREIGN PATENT DOCUMENTS

AU    199642145    8/1996
AU    199928098    7/1999

(Continued)

OTHER PUBLICATIONS

Adeyemi et al, Analgesic and anti-inflammatory effects of the aqueous extract of leaves of Persea Americana Mill (lauraceae), Fitoterapia 73 (2002) 375-380.*
Nordal et al, Isolation of mannoheptulose and identification of its phosphate in avocado leaves, Meddelelser fra Norsk Farmaceutisk Selskap (1955), 17, 207-13.*
Wan et al, Dietary supplementation with 2-deoxy-d-glucose improves cardiovascular and neuroendocrine stress adaptation in rats; Am. J. Physiol Heart Circ. Physiol; Bearing dates of Oct. 10, 2003.*
Ojewole et al, Anticonvulsant effect of *Persea americana* Mill (Lauraceae) (Avocado) leaf aqueous extract in mice. Phytotherapy research : PTR, (Aug. 2006) vol. 20, No. 8, pp. 696-700.*

(Continued)

*Primary Examiner* — Qiuwen Mi
(74) *Attorney, Agent, or Firm* — Mars, Incorporated; Colleen Kramer

(57) ABSTRACT

A method for decreasing inflammation and stress in a mammal comprising; administration to a mammal a composition comprising a glucose anti-metabolite; and wherein said composition comprises amounts of the glucose anti-metabolite sufficient to lower a level of a C-reactive protein in the blood of the mammal subsequent to administration of the glucose anti-metabolite.

24 Claims, No Drawings

(56) References Cited

U.S. PATENT DOCUMENTS

| | | |
|---|---|---|
| 5,322,686 A | 6/1994 | Grahn et al. |
| 5,344,824 A | 9/1994 | Ohkuma |
| 5,389,389 A | 2/1995 | Beck |
| 5,413,960 A | 5/1995 | Dobrogosz et al. |
| 5,445,828 A | 8/1995 | Pozzi et al. |
| 5,451,400 A | 9/1995 | Stern et al. |
| 5,474,932 A | 12/1995 | Bengmark et al. |
| 5,484,721 A | 1/1996 | Ors et al. |
| 5,501,857 A | 3/1996 | Zimmer |
| 5,501,868 A | 3/1996 | Collings |
| 5,516,684 A | 5/1996 | Saito et al. |
| 5,518,733 A | 5/1996 | Lamothe et al. |
| 5,531,988 A | 7/1996 | Paul |
| 5,538,743 A | 7/1996 | Heinemann et al. |
| 5,540,945 A | 7/1996 | Ikushima |
| 5,569,634 A | 10/1996 | Miller et al. |
| 5,578,302 A | 11/1996 | Brassart et al. |
| 5,582,643 A | 12/1996 | Takei et al. |
| 5,603,930 A | 2/1997 | Brassart |
| 5,629,017 A | 5/1997 | Pozzi et al. |
| 5,633,012 A | 5/1997 | Ford |
| 5,645,830 A | 7/1997 | Reid |
| 5,698,437 A | 12/1997 | Matsuda et al. |
| 5,726,161 A | 3/1998 | Whistler |
| 5,728,380 A | 3/1998 | Allen et al. |
| 5,733,540 A | 3/1998 | Lee |
| 5,756,088 A | 5/1998 | Matsuura et al. |
| 5,766,520 A | 6/1998 | Bronshtein |
| 5,785,990 A | 7/1998 | Langrehr |
| 5,814,338 A | 9/1998 | Veronesi |
| 5,824,779 A | 10/1998 | Koegel et al. |
| 5,849,327 A | 12/1998 | Berliner et al. |
| 5,853,697 A | 12/1998 | Strober et al. |
| 5,854,067 A | 12/1998 | Newgard et al. |
| 5,858,356 A | 1/1999 | Wolf et al. |
| 5,871,794 A | 2/1999 | Brito |
| 5,871,802 A | 2/1999 | Gao |
| 5,894,029 A | 4/1999 | Brown et al. |
| 5,910,447 A | 6/1999 | Lawrence et al. |
| 5,939,117 A | 8/1999 | Chen |
| 5,952,021 A | 9/1999 | Santus |
| 5,952,033 A | 9/1999 | Anantharaman et al. |
| 5,962,043 A | 10/1999 | Jones |
| 5,968,569 A | 10/1999 | Cavadini et al. |
| 5,976,579 A | 11/1999 | McLean |
| 6,007,808 A | 12/1999 | DeHaen et al. |
| 6,010,725 A | 1/2000 | Meister et al. |
| 6,033,888 A | 3/2000 | Batich et al. |
| 6,042,857 A | 3/2000 | Jones et al. |
| 6,063,414 A | 5/2000 | Jones et al. |
| 6,077,530 A | 6/2000 | Weinstein et al. |
| 6,080,401 A | 6/2000 | Reddy et al. |
| 6,083,520 A | 7/2000 | Toneby |
| 6,117,477 A | 9/2000 | Paluch et al. |
| 6,133,323 A | 10/2000 | Hayek |
| 6,156,355 A | 12/2000 | Shields et al. |
| 6,190,591 B1 | 2/2001 | van Lengerich |
| 6,254,886 B1 | 7/2001 | Fusca et al. |
| 6,277,370 B1 | 8/2001 | Vavaliere Ved. Vesely et al. |
| 6,309,666 B1 | 10/2001 | Hatano et al. |
| 6,310,090 B1 | 10/2001 | Hayek |
| 6,355,242 B1 | 3/2002 | Allison et al. |
| 6,358,555 B1 | 3/2002 | Takahashi |
| 6,365,148 B1 | 4/2002 | Kim et al. |
| 6,375,956 B1 | 4/2002 | Hermelin et al. |
| 6,394,803 B1 | 5/2002 | Salz et al. |
| 6,406,853 B1 | 6/2002 | Spindler |
| 6,451,341 B1 | 9/2002 | Slaga et al. |
| 6,500,463 B1 | 12/2002 | van Lengerich |
| 6,506,389 B2 | 1/2003 | Leer et al. |
| 6,544,568 B2 | 4/2003 | La Droitte et al. |
| 6,586,027 B2 | 7/2003 | Axelrod |
| 6,588,180 B2 | 7/2003 | Heath |
| 6,592,863 B2 | 7/2003 | Fuchs et al. |
| 6,596,946 B2 | 7/2003 | Yagi et al. |
| 6,607,905 B1 | 8/2003 | Luquet |
| 6,620,440 B1 | 9/2003 | Hsia |
| 6,624,162 B2 | 9/2003 | Uchida et al. |
| 6,681,935 B1 | 1/2004 | Lewis |
| 6,713,083 B1 | 3/2004 | McGregor et al. |
| 6,723,358 B1 | 4/2004 | van Lengerich |
| 6,737,089 B2 | 5/2004 | Wadsworth |
| 6,746,672 B2 | 6/2004 | O'Sullivan |
| 6,767,573 B1 | 7/2004 | Dixon et al. |
| 6,780,433 B2 | 8/2004 | Cochran et al. |
| 6,797,266 B2 | 9/2004 | Naidu |
| 6,802,422 B2 | 10/2004 | Kalvelage et al. |
| 6,827,957 B2 | 12/2004 | Paluch et al. |
| 6,835,397 B2 | 12/2004 | Lee et al. |
| 6,893,662 B2 | 5/2005 | Dittmar et al. |
| 6,905,679 B1 | 6/2005 | Schiffrin et al. |
| 6,911,217 B1 | 6/2005 | Gren et al. |
| 6,932,990 B2 | 8/2005 | Konishi |
| 6,939,560 B2 | 9/2005 | Shen et al. |
| 6,974,594 B2 | 12/2005 | Ko et al. |
| 6,979,675 B2 | 12/2005 | Tidmarsh |
| 6,991,819 B2 | 1/2006 | Pannevis et al. |
| 7,008,648 B2 | 3/2006 | Corley et al. |
| 7,037,708 B1 | 5/2006 | Runge et al. |
| 7,081,478 B2 | 7/2006 | Hauptmann et al. |
| 7,097,831 B1 | 8/2006 | Bengs |
| 7,115,297 B2 | 10/2006 | Stillman et al. |
| 7,122,370 B2 | 10/2006 | Porubcan |
| RE39,436 E | 12/2006 | Spindler et al. |
| 7,150,986 B2 | 12/2006 | Kato et al. |
| 7,179,460 B2 | 2/2007 | Dennin et al. |
| 7,186,545 B2 | 3/2007 | Collins et al. |
| 7,189,390 B2 | 3/2007 | Zink et al. |
| 7,195,906 B2 | 3/2007 | Collins et al. |
| 7,201,923 B1 | 4/2007 | van Lengerich et al. |
| 7,229,818 B2 | 6/2007 | Porubcan |
| 7,235,276 B2 | 6/2007 | Allen et al. |
| 7,235,395 B2 | 6/2007 | Stadler et al. |
| 7,381,406 B2 | 6/2008 | Zink et al. |
| 7,390,519 B2 | 6/2008 | Collins et al. |
| 7,427,398 B2 | 9/2008 | Baillon et al. |
| 7,498,162 B2 | 3/2009 | Germond et al. |
| 7,544,497 B2 | 6/2009 | Sinclair et al. |
| 7,547,527 B2 | 6/2009 | Baur et al. |
| 7,550,285 B2 | 6/2009 | Schiffrin et al. |
| 7,579,030 B2 | 8/2009 | Domingues et al. |
| 7,647,098 B2 | 1/2010 | Prichep |
| 7,674,808 B2 | 3/2010 | Bueno Calderon et al. |
| 7,687,077 B2 | 3/2010 | Khoo |
| 7,687,085 B2 | 3/2010 | Hayashi et al. |
| 7,700,141 B2 | 4/2010 | Baillon et al. |
| 7,700,315 B2 | 4/2010 | Arigoni et al. |
| 7,771,982 B2 | 8/2010 | Zink et al. |
| 7,785,635 B1 | 8/2010 | Boileau et al. |
| 7,833,554 B2 | 11/2010 | Piccirilli et al. |
| 7,838,057 B2 | 11/2010 | Schmidt et al. |
| 7,842,329 B2 | 11/2010 | Saylock et al. |
| 7,906,112 B2 | 3/2011 | Boileau et al. |
| 7,910,144 B2 | 3/2011 | Ballevre et al. |
| 7,935,334 B2 | 5/2011 | Lin |
| 7,960,605 B2 | 6/2011 | Zhao-Wilson |
| 7,998,473 B2 | 8/2011 | Boileau et al. |
| 8,030,279 B2 | 10/2011 | Joullie |
| 8,034,601 B2 | 10/2011 | Boileau et al. |
| 8,057,840 B2 | 11/2011 | Harrison et al. |
| 8,092,608 B2 | 1/2012 | Rochat et al. |
| 8,101,170 B2 | 1/2012 | Plail et al. |
| 8,142,810 B2 | 3/2012 | Sunvold |
| 8,263,146 B2 | 9/2012 | Bengtsson et al. |
| 8,313,757 B2 | 11/2012 | Van Lengerich |
| 8,329,190 B2 | 12/2012 | Vidal et al. |
| 8,394,370 B2 | 3/2013 | Garcia |
| 8,486,389 B2 | 7/2013 | Sidhu et al. |
| 8,524,304 B2 | 9/2013 | Prakash et al. |
| 8,540,980 B2 | 9/2013 | London et al. |
| 8,557,764 B2 | 10/2013 | Newell et al. |
| 8,563,522 B2 | 10/2013 | Pitha et al. |
| 8,637,495 B2 | 1/2014 | Waldron et al. |
| 8,663,729 B2 | 3/2014 | Hayek et al. |

(56) References Cited

U.S. PATENT DOCUMENTS

| | | |
|---|---|---|
| 8,691,303 B2 | 4/2014 | Sunvold et al. |
| 8,722,112 B2 | 5/2014 | Zicker et al. |
| 8,728,559 B2 | 5/2014 | Hayek et al. |
| 8,771,675 B2 | 7/2014 | Zink et al. |
| 8,802,158 B2 | 8/2014 | Boileau et al. |
| 8,802,179 B2 | 8/2014 | Miller |
| 8,808,770 B2 | 8/2014 | Henderson et al. |
| 8,809,035 B2 | 8/2014 | Boileau et al. |
| 8,865,197 B2 | 10/2014 | Tandler et al. |
| 8,877,178 B2 | 11/2014 | Boileau et al. |
| 8,894,991 B2 | 11/2014 | Boileau et al. |
| 8,900,569 B2 | 12/2014 | Boileau et al. |
| 8,916,145 B2 | 12/2014 | Mercenier et al. |
| 8,962,007 B2 | 2/2015 | Perez et al. |
| 9,089,576 B2 | 7/2015 | Piccirilli et al. |
| 9,119,843 B2 | 9/2015 | Chen et al. |
| 9,192,177 B2 | 11/2015 | Boileau et al. |
| 2002/0022019 A1 | 2/2002 | Laulund |
| 2002/0035071 A1* | 3/2002 | Pitha et al. ............ 514/23 |
| 2002/0119237 A1 | 8/2002 | Hevey |
| 2003/0049240 A1 | 3/2003 | Ballevre et al. |
| 2003/0060503 A1 | 3/2003 | Hamilton |
| 2003/0092669 A1 | 5/2003 | Chapnick |
| 2003/0104090 A1 | 6/2003 | Levy et al. |
| 2003/0113306 A1 | 6/2003 | Collins et al. |
| 2003/0143293 A1 | 7/2003 | Shushunov |
| 2003/0157166 A1 | 8/2003 | Chen |
| 2003/0170217 A1 | 9/2003 | Collins et al. |
| 2003/0170355 A1 | 9/2003 | Glazier et al. |
| 2003/0190314 A1 | 10/2003 | Campbell et al. |
| 2003/0194423 A1 | 10/2003 | Torney et al. |
| 2004/0001817 A1 | 1/2004 | Giampapa et al. |
| 2004/0022882 A1 | 2/2004 | Picirilli |
| 2004/0047896 A1 | 3/2004 | Malnoe et al. |
| 2004/0161422 A1 | 8/2004 | Ranganathan |
| 2004/0167229 A1* | 8/2004 | Bakker-Arkema et al. ... 514/675 |
| 2004/0228933 A1 | 11/2004 | Chapnick |
| 2004/0234579 A1 | 11/2004 | Finke |
| 2004/0253357 A1 | 12/2004 | De Zarate |
| 2004/0265279 A1 | 12/2004 | Dinan et al. |
| 2005/0013849 A1 | 1/2005 | Lemaure |
| 2005/0074519 A1 | 4/2005 | Bartnick et al. |
| 2005/0079244 A1 | 4/2005 | Giffard et al. |
| 2005/0084479 A1 | 4/2005 | Corthesy et al. |
| 2005/0100617 A1 | 5/2005 | Malnoe et al. |
| 2005/0106131 A1 | 5/2005 | Breton et al. |
| 2005/0112259 A1 | 5/2005 | Qvyjt |
| 2005/0152884 A1 | 7/2005 | Boileau et al. |
| 2005/0153018 A1 | 7/2005 | Ubbink et al. |
| 2005/0164978 A1 | 7/2005 | Chapnick et al. |
| 2005/0180961 A1 | 8/2005 | Pecquet et al. |
| 2005/0208163 A1 | 9/2005 | Brovelli et al. |
| 2005/0249837 A1* | 11/2005 | Massimino et al. ............ 426/52 |
| 2005/0249841 A1 | 11/2005 | Hayek et al. |
| 2005/0266438 A1 | 12/2005 | Spindler |
| 2005/0281910 A1 | 12/2005 | Schiffrin et al. |
| 2006/0002909 A1 | 1/2006 | Takeda |
| 2006/0008511 A1 | 1/2006 | Lin et al. |
| 2006/0070895 A1 | 4/2006 | Khawaja |
| 2006/0088517 A1 | 4/2006 | Kriegler |
| 2006/0099196 A1 | 5/2006 | Breton et al. |
| 2006/0100162 A1* | 5/2006 | Pitha et al. ............ 514/23 |
| 2006/0116330 A1 | 6/2006 | Pitha |
| 2006/0121015 A1 | 6/2006 | Collins et al. |
| 2006/0147962 A1 | 7/2006 | Jones et al. |
| 2006/0165670 A1 | 7/2006 | Berr et al. |
| 2006/0228448 A1 | 10/2006 | Boileau et al. |
| 2006/0228459 A1 | 10/2006 | Tribelhorn et al. |
| 2006/0263416 A1 | 11/2006 | Brent, Jr. |
| 2007/0009577 A1 | 1/2007 | Mankovitz |
| 2007/0031441 A1 | 2/2007 | Collins et al. |
| 2007/0082107 A1 | 4/2007 | Aimutis et al. |
| 2007/0098744 A1 | 5/2007 | Knorr et al. |
| 2007/0116853 A1 | 5/2007 | Krohn et al. |
| 2007/0122531 A1 | 5/2007 | Considini |
| 2007/0123460 A1 | 5/2007 | Chang et al. |
| 2007/0129428 A1 | 6/2007 | Richelle et al. |
| 2007/0149466 A1 | 6/2007 | Milburn et al. |
| 2007/0160589 A1 | 7/2007 | Mattson et al. |
| 2007/0166295 A1 | 7/2007 | Schildgen et al. |
| 2007/0178078 A1 | 8/2007 | Khoo |
| 2007/0190171 A1 | 8/2007 | Yamka et al. |
| 2007/0218164 A1 | 9/2007 | Stojanovic |
| 2007/0231371 A1 | 10/2007 | Pan et al. |
| 2007/0231414 A1 | 10/2007 | Aoki et al. |
| 2007/0269515 A1 | 11/2007 | Henriksen et al. |
| 2007/0269553 A1 | 11/2007 | Le et al. |
| 2007/0280964 A1 | 12/2007 | Knorr et al. |
| 2007/0286935 A1 | 12/2007 | Grigorov et al. |
| 2008/0044481 A1 | 2/2008 | Harel |
| 2008/0050354 A1 | 2/2008 | Garault et al. |
| 2008/0050355 A1 | 2/2008 | Vaslin |
| 2008/0053490 A1 | 3/2008 | Clark et al. |
| 2008/0107699 A1 | 5/2008 | Spigelman et al. |
| 2008/0145341 A1 | 6/2008 | Myatt et al. |
| 2008/0214479 A1 | 9/2008 | Pitha |
| 2008/0241226 A1 | 10/2008 | Abeln et al. |
| 2008/0260696 A1 | 10/2008 | Massimino et al. |
| 2008/0260866 A1 | 10/2008 | Massimino et al. |
| 2008/0279786 A1 | 11/2008 | Cash |
| 2008/0280274 A1 | 11/2008 | Freisen et al. |
| 2008/0305210 A1 | 12/2008 | Petersen |
| 2008/0311226 A1 | 12/2008 | Yamka et al. |
| 2008/0317905 A1 | 12/2008 | Yamka et al. |
| 2009/0252834 A1 | 10/2009 | Hayek et al. |
| 2009/0263542 A1 | 10/2009 | Lin et al. |
| 2009/0274796 A1 | 11/2009 | Yamka et al. |
| 2009/0324761 A1 | 12/2009 | Khoo et al. |
| 2010/0003369 A1 | 1/2010 | Ter Haar et al. |
| 2010/0112003 A1 | 5/2010 | Collins et al. |
| 2010/0150870 A1 | 6/2010 | Young et al. |
| 2010/0203225 A1 | 8/2010 | Kerr et al. |
| 2010/0233320 A1 | 9/2010 | Sunvold et al. |
| 2010/0316769 A1 | 12/2010 | Czarnecki-Maulden et al. |
| 2011/0117068 A1 | 5/2011 | Lang et al. |
| 2011/0274676 A1 | 11/2011 | Farmer et al. |
| 2012/0115798 A1 | 5/2012 | Massimino et al. |
| 2012/0282373 A1 | 11/2012 | Luhadiya et al. |
| 2012/0283197 A1 | 11/2012 | Luhadiya et al. |
| 2013/0183255 A1 | 7/2013 | Saunois et al. |
| 2014/0274920 A1 | 9/2014 | Davenport |
| 2014/0348975 A1 | 11/2014 | Davenport et al. |
| 2014/0348986 A1 | 11/2014 | Beyer et al. |
| 2014/0349002 A1 | 11/2014 | Beyer |
| 2015/0132420 A1 | 5/2015 | Villagran et al. |
| 2015/0208679 A1 | 7/2015 | Mir et al. |

FOREIGN PATENT DOCUMENTS

| | | |
|---|---|---|
| CA | 1300538 | 5/1992 |
| CA | 2093287 | 10/1993 |
| CA | 2256256 | 6/2000 |
| CA | 2569249 | 11/2005 |
| DE | 3715070 A1 | 11/1988 |
| DE | 4018392 A1 | 12/1991 |
| DE | 10217970 | 11/2003 |
| EP | 0168112 | 1/1986 |
| EP | 0181170 | 5/1986 |
| EP | 0212746 | 3/1987 |
| EP | 0212747 | 3/1987 |
| EP | 0298605 | 1/1989 |
| EP | 0391416 | 10/1990 |
| EP | 0399819 | 11/1990 |
| EP | 0563934 | 10/1993 |
| EP | 0627173 | 12/1994 |
| EP | 0850569 | 7/1998 |
| EP | 1547466 | 6/2005 |
| EP | 1637041 | 3/2006 |
| EP | 1806056 | 7/2007 |
| EP | 1806057 | 7/2007 |
| FR | 2615203 | 11/1988 |
| FR | 2663198 | 12/1991 |
| GB | 1190387 | 5/1970 |
| GB | 1503094 | 3/1978 |

(56) References Cited

FOREIGN PATENT DOCUMENTS

| | | |
|---|---|---|
| GB | 1595054 | 8/1981 |
| GB | 2241421 | 9/1990 |
| GB | 2252228 | 8/1992 |
| JP | S59213368 | 12/1984 |
| JP | S6024153 | 2/1985 |
| JP | S6297221 | 5/1987 |
| JP | S62201823 | 9/1987 |
| JP | 03076561 | 4/1991 |
| JP | H06256170 | 9/1994 |
| JP | H08242763 | 9/1996 |
| JP | 2000191519 | 7/2000 |
| JP | 2001278781 | 10/2001 |
| JP | 2001309753 | 11/2001 |
| JP | 2007117083 | 11/2001 |
| JP | 1995378530 | 8/2003 |
| JP | 2004173675 | 6/2004 |
| JP | 2006055145 | 3/2006 |
| KR | 20020050048 | 6/2002 |
| KR | 20040024774 | 3/2004 |
| RU | 2086248 | 8/1997 |
| RU | 2123343 | 12/1998 |
| RU | 2388320 | 5/2010 |
| RU | 2407401 | 12/2010 |
| WO | 8808452 | 11/1988 |
| WO | 8905849 | 6/1989 |
| WO | 9001335 | 2/1990 |
| WO | 9117672 | 11/1991 |
| WO | 9302558 | 2/1993 |
| WO | 9404180 | 3/1994 |
| WO | 9421284 | 9/1994 |
| WO | 9503809 | 2/1995 |
| WO | 9507090 | 3/1995 |
| WO | 9709448 | 3/1997 |
| WO | 9716198 | 5/1997 |
| WO | 9720577 | 6/1997 |
| WO | 9819668 | 5/1998 |
| WO | 9827967 | 7/1998 |
| WO | 9854982 | 12/1998 |
| WO | 9909839 | 3/1999 |
| WO | 9930576 | 6/1999 |
| WO | 9952511 | 10/1999 |
| WO | WO 99/51108 A1 | 10/1999 |
| WO | 0006127 | 2/2000 |
| WO | 0112164 | 2/2001 |
| WO | 01/90311 | 11/2001 |
| WO | 03045356 | 6/2003 |
| WO | 03/075676 | 9/2003 |
| WO | 2004074496 | 9/2004 |
| WO | WO 2004/100670 A1 | 11/2004 |
| WO | WO 2005/115421 A | 4/2005 |
| WO | 2005070232 | 8/2005 |
| WO | 2005092116 | 10/2005 |
| WO | WO 2005/105123 A | 11/2005 |
| WO | 2007060539 | 5/2007 |
| WO | WO 2007/057439 A | 5/2007 |
| WO | 2007/126990 | 11/2007 |
| WO | 2007137808 | 12/2007 |

OTHER PUBLICATIONS

Appelboom, Symptoms modifying effect of avocado/soybean unsaponifiables (ASU) in knee osteoarthritis. A double blind, prospective, placebo-controlled study. Scandinavian journal of rheumatology, (2001) vol. 30, No. 4, pp. 242-247.*

Adeyemi et al, "Analgesic and Anti-Inflammatory Effects of the Aqueous Extract Leaves of Persea Americana Mill (Lauraceae)" Fitoterapia, IDB Holding, Milan, IT, vol. 73, No. 5, Aug. 1, 2002, pp. 375-380, XP002318086.

"Avocado sugars are effective inducer of cutaneous defensive functions" Journal of the American Academy of Dermatology, C V Mosby, St Louis MO, US, vol. 50, No. 2, Feb. 1, 2007 p. AB84, XP005937005.

Burger et al., "Cardiomyopathy in Ostriches (*Struthio Camelus*) Due to Avocado 9*Persea americana* Var. *guatemalensis*) Intoxication", *Journal of the South African Veterinary Association*, vol. Jaargang 65 No. 2, Jun./Jun. 1994.

Byung Pal Yu et al., "Modulation of Aging Processes by Dietary Restriction", *CRC Press*, Boca Raton (1994).

Cullen et al., "Inhibition of glucose metabolism in pancreatic cancer induces cytotoxicity via metabolic oxidative stress" Gastroenterology, vol. 128, No. 4 supp. 2, Apr. 2005 pp. A483, XP002495963.

Database Embase (Online) Elsevier Science Publishers, Amsterdam, NL, Nov. 2004, Carranza J et al, "Lower quantities of avocado as daily source of monounsaturated fats: Effect on serum and membrane lipids, endothelial function, platelet aggregation and C-reactive protein in patients with metabolic syndrome" XP002485347.

Ekor et al., "Protective effect of the methanolic leaf extract of *Persea anericana* (avocado) against paracetamol-induced acute hepatotoxicity in rats" International Jornal of Pharmacology, Asian Network for Scientific Information, vol. 2, No. 4, Jan. 1, 2006, pp. 416-420, XP001538905.

F. B. La Forge, Absorption and Effect of Ingested Mannoheptulose, *Nutrition Reviews*, vol. 27, No. 7 1969.

Facchini et al., Insulin Resistance as a Predictor of Age-Related Diseases, *The Journal of Clinical Endocrinology & Metabolism*, 86(8): 3574-3578, 2001.

Francesconi et al., "5-Thio-D-Glucose: Hypothermic Responses in Mice", *Am. J. Physiology*, 239(3) R214-R218, 1980.

Guo et al., "In Vivo 2-Deoxyglucose Administration Preserves Glucose and Glutamate Transport and Mitochondrial Function in Cortical Synaptic Terminals After Exposure to Amyloid Beta-Peptide and Iron: Evidence for a Stress Response" Experimental Neurology, Academic Press, vol. 166. No. 1, Jan. 1, 2000, XP008056810 pp. 173-179.

Kalant et al., "Effect of Diet Restriction on Glucose Metabolism and Insulin Responsiveness in Aging Rats", Mechanisms of Ageing and Development, 46 (1988) 89-104.

Kealy et al., "Effects of Diet Restriction on Life Span and Age-Related Changes in Dogs", *JAVMA*, vol. 220, No. 9, May 1, 2002.

Koizumi et al., "Influences of Dietary Restriction and Age on Liver Enzyme Activities and Lipid Peroxidation in Mice" 1987 *American Institute of Nutrition*, Jul. 1986.

Kurata et al., "Structural Evaluation of Glucose Analogues on Feeding Elicitation in Rat", *Metabolism*, vol. 38, No. 1 (Jan.), 1989: pp. 46-51.

Lane et al., "2-Deoxy-D-Glucose Feeding in Rats Mimics Physiologic Effects of Calorie Restriction", *Journal of Anti-Aging Medicine*, vol. 1, No. 4, 1998.

Lane et al., "Calorie Restriction in Nonhuman Primates: Implications for Age-Related Disease Risk", *Journal of Anti-Aging Medicine*, vol. 1, No. 4, 1998.

Lane et al., "Calorie Restriction Lowers Body Temperature in Rhesus Monkeys, Consistent With a Postulated Anti-Aging Mechanism in Rodents", *Proc. Natl. Acad. Sci.*, vol. 93 pp. 4159-4164, Apr. 1996.

Lawrence Fishbein et al., Biological Effects of Dietary Restriction, *Springer-Verlag*, 1991.

Liu et al., "'Hass' Avocado Carbohydrate Fluctuations. I. Growth and Phenology", *J. Amer. Soc. Hort. Sci.* 124(6): 671-675. 1999.

Liu et al., "'Hass' Avocado Carbohydrate Fluctuations. II. Fruit Growth and Ripening", *J. Amer. Soc. Hort. Sci.*, 124(6): 676-681. 1999.

Liu et al., "Postulated Physiological Roles of the Seven-Carbon Sugars, Mannoheptulose, and Perseitol in Avocado", *J. Amer. Soc. Hort. Sci.*, 127 (1): 108-114, 2002.

Masoro et al., "Dietary Restriction Alters Characteristics of Glucose Fuel Use", *Journal of Geronotology*, Biological Sciences 1992, vol. 47, No. 6 B202-B208.

McKay et al., "The Effect of Retarded Growth Upon the Length of Life Span and Upon the Ultimate Body Size", *J. Nutr.*, vol. 10, pp. 63-79 (1935).

Meyer et al., "Effects of D-mannoheptulose and Its Hexaacetate Ester on Hormonal Secretion From the Perfused Pancreas", *International Journal of Molecular Medicine*, 6: 143-152, 2000.

(56) References Cited

OTHER PUBLICATIONS

Naveh et al., "Defatted Avocado Pulp Reduces Body Weight and Total Hepatic Fat but Increases Plasma Cholesterol in Male Rats Fed Diets wWth Cholesterol", *American Society for Nutritional Sciences*, 2002, pp. 2015-2018.
Nutrigenomics New Zealand Sutton et al, "Considerations for successful development and launch of personalized nutrigenomic foods" Mutation Research, Amsterdam, NL, vol. 622. No. 1-2, Aug. 8, 2007, pp. 117-121, XP022191854.
Poehlman et al., "Caloric Restriction Mimetics: Physical Activity and Body Composition Changes", *Journals of Geronotology*: Series A 2001, vol. 56A (Special Issue I): 45-54.
Ramsey et al., "Dietary Restriction and Aging in Rehesus Monkeys: The University of Wisconsin Study", *Experimental Gerontology*, 35 (2000) 1131-1149.
Rezek et al., "Glucose Antimetabolites and Hunger", 106: 143-157, 1975.
Roth et al., "Caloric Restriction in Primates and Relevance to Humans", *Laboratory of Neurosciences, Geronotology Research Center, National Institute on Aging, National Institutes of Health Pages*, 307-315, 2001.
Scarbrough et al. "2-deoxy-D-glucose and 17-(allylamino)-17-demethoxygeldanamycin enhances toxicity as well as increases parameters indicative od oxidative stress" Free Radical Biology and Medicine, Elsevier Science, vol. 43, No. suppl. 1, Nov. 14, 2007, p. S59, XP009105389.
Sener et al., "D-mannoheptulose Uptake and Its Metabolic and Secretory Effects in Human Pancreatic Islets", *International Journal of Molecular Medicine*, 6: 617-620, 2000.
Shaw et al., "High Performance Liquid Chromatographic Analysis of d-manno-Heptulose, Perseitol, Glucose, and Fructose in Avocado Cultivars", *J. Agric. Food Chem*. 1980, 28, 379-382.
Simons et al. "2-deoxy-D-gulcose (2DG) enhances cisplatin cytotoxicity in human head and neck cancer cells via metabolic oxidative stress" Free Radical Biology and Medicine, vol. 41, No. suppl. 1, Nov. 15, 2006, pp. S112-S-113, XP009105143.
Sakata et al., "Feeding Modulation by Pentose and Hexose Analogues[1-3]", *Am. J. Clin Nutr* 1992: 55:272S-7S.
Viktora, et al., "Effect of Ingested Mannopheptulose in Animals and Man", *Metabolism*, 1969, vol. 18, No. 2, pp. 87-102.
Weindruch et al., "The Retardation of Aging and Disease by Dietary Restriction", *Charles S. Thomas* (1988).
International Search Report received in connection with PCT/IB2008/050382, mailed on Oct. 7, 2008.
A. Nordal, et al., "Isolation of Mannoheptulose and Identification of its Phosphate in Avocado Leaves", J. Am. Chem. Soc., vol. 76, No. 20, pp. 5054-5055, 1954.
Ridker et al., "C-Reactive Protein, the Metabolic Syndrome, and Risk of Incident Cardiovascular Events: An 8-Year Follow-up of 14,719 Initially Healthy American Women", Circulation, vol. 107, No. 3, pp. 391-397, Jan. 2003.
Roe et al., "The Utilization of D-mannohepulose (d-manno-ketoheptose) by Adult Rabbits", Biol. Chem., vol. 112, pp. 443-449, 1936.
Blatherwick et al., "Metabolism of D-mannoheptulose. Excretion of the Sugar After Eating Avocado", J. Biol. Chem., vol. 133, pp. 643-650, 1940.
Koh et al., "Effects of Mannoheptulose on Lipid Metabolism of Rats", J. Nutr., vol. 104, pp. 1227-1233, 1974.
Issekutz, Jr. et al., "Effect of Mannoheptulose on Glucose Kinetics in Normal and Glucocorticoid Treated Dogs", Life Sciences, vol. 16, pp. 635-643, 1977.
Archived pages from HTTP://web.archive.org for http://medtechnologies.com dated Jan. 2003.
Archived pages from HTTP://web.archive.org for http://medtechnologies.com dated Feb. 2003.
Blue Buffalo Life Protection Formula_package.pdf, http//www.bluebuff.com/products/dogs/lp-adult-chick.shtml Information accessed Feb. 3, 2009.
Breeders Choice, AvoDERM product brochures http://www.breeders-choice.com/about/brochures.htm, Information accessed Feb. 3, 2009.
Natures Logic Natural Chicken Dinner Fare FROZEN_package.pdf http://www.natureslogic.com/products/dp_rf_chi.html, Information accessed Feb. 3, 2009.
Natures Logic Natural Chicken Meal_package.pdf http://www.natureslogic.com/products/dp_dry_chi.html, Information accessed Feb. 3, 2009.
Publication downloaded from http://en.wikipedia.org/wiki/Noni on May 4, 2009, 9 pages.
Ashcroft, et al., "Glucose Metabolism in Mouse Pancreatic Islets", Biochem. J. (1970), 118, pp. 143-154.
Au, et al., "Avocado Soybean Unsaponifiables (ASU) suppress TNF-a, IL-lb, cox-2, iNOS Gene Expression, and Prostaglanding E2 and Nitric Ocide Production in Articular Chondrocytes and Monocyte/Macrophages", Osteoarthritis and Cartilage, 2007, 15, 18 pages.
Balkau, et al., Diabetes Obes. Metab., 1 (Suppl. 1), pp. S23-31, 1999.
Barge, "Avocados May Help Prevent Oral Cancer, OSU Study Shows", Journal of Dental Hygiene, vol. 82, No. 2, Apr. 2008, 3 pp.
Board, et al., "High KM Glucose Phosphorylating (Glucokinase) Activities in a Range of Tumor Cell Lines and Inhibition of Rates of Tumor Growth by the Specific Enzyme Inhibitor Mannoheptulose", Cancer Research, vol. 55, pp. 3278-3285, Aug. 1995.
Brai, et al., "Hypoglycemic and Hypochloesterolemic Potential of Persea Americana Leaf Extracts", J. Med. Food, 2007, pp. 356-360.
Brown, et al., "Glucose Phosphorylation is Essential for the Turnover of Neutral Lipid and the Second Stage Assembly of Triacylglycerol-Rich ApoB-Containing Lipoproteins in Primary Hepatocyte Cultures", American Heart Association, Inc., 1999, pp. 321-329.
Chan, et al., "Ultra Structural and Secretory Heterogeneity of fa/fa (Zucker) Rat Islets", Molecular and Cellular Endocrinology, 136, 1998, pp. 119-129.
Conde, et al., "OeMST2 Encodes a monosaccharid Transporter Expressed throughout Olive Fruit Maturation", Plant Cell Physiol, 48(9), pp. 1299-1308, 2007.
Ernst, "Avocado-Soybean Unsaponifiables (ASU) for Osteoarthritis-A systemic Review", Clin. Rheumatol., 2003, 22, pp. 285-288.
Frech, et al., "The Utility of Nutraceuticals in teh Treatment of Osteoarthritis", Current Rheumatology Reports, 2007, 9, pp. 25-30.
Gallagher, et al., "The Effects of Traditional Antidiabetic Plants on In Vitro Glucose Diffusion", Nutrition Research, 23 (2003), pp. 413-424.
Gondwe, "Effects of Oersea Americana Mill (Lauraceae) Ethanolic Leaf Extract on Blood Glucose and Kidney Function in Streptozotocin-Induced Diabetic Rats and on Kidney Cell Lines of the Proximal (LLC-PK1) and Distal Tubules (MDBK)", Methods Find Exp Clin. Pharmacol., 2008, 30(1), pp. 25-35.
Henrotin, et al., "Pharmaceutical and Nutraceutical Management of Canine Osteoarthritis: Present and Future Perspectives", The Veterinary Journal, 170 (2005), pp. 113-123.
Johnson, et al., "Glucose-Dependent Modulation in Insulin Secretion and Intracellular Calcium Ions by GKA50, a Glucokinase Activator", Diabetes, vol. 56, Jun. 2007, pp. 1694-1702.
Kappler-Tanudyaya, et al., "Combination of Biotransformation and Chromatography for the Isolation and Purification of Mannoheptulose", Biotechnology J. 2007, 2, 692-699.
Katzmarzyk, "The Metabolic Syndrome: An Introduction", Appl. Physiol. Nutr. Metab., 32, pp. 1-3 (2007).
Kibenge, et al., "Identification of Biochemical Defects in Pancreatic Islets of fa/fa Rats", Obesity Research, 3(2), pp. 171-178, Mar. 1995.
Klain, et al., "Mannoheptulose and Fatty Acid Synthesis in the Rat", The Joumal of Nutrition, pp. 473-477, 1974.
Langhans, et al., "Changes in Food Intake and Meal Patterns Following Injection of D-Mannoheptulose in Rats", Behavioral and Neural Biology, 38, pp. 269-286 (1983).
Maklashina, et al., "Is Defective Electron Transport at the Hub of Aging", Aging Cell, vol. 3, 21-27, 2004.
Mermelstein, Food Technology, 51(10), p. 96, 1997.
Pelicano, et al., "Glycolysis Inhibition for Anticancer Treatment", Oncogene, 2006, 25, pp. 4633-4646.
Rezek, J. Nutr. 106:143-157, 1972.

(56) References Cited

OTHER PUBLICATIONS

Rezek, et al., "Insulin Dependence of Paradoxical Overeating: Effect of Mannoheptulose, Somatostatin, and cycloheximide", The American Physiological Society, 1979, E205-E211.

Robey, et al., "Akt, Hexokinase, mTOR: Targeting Cellular Energy Metabloism for Cancer Therapy", Drug Discovery Today: Disease Mechanisms, vol. 2, No. 2, 2005, pp. 239-246.

Roth, Ann. Ny Acad. Aci., 928: 305-315, 2001.

Scruel, et al., "Interference of D-Mannoheptuloase with D-Glucose phosphorylation, Metabolism, and Functional Effects: Comparison between Liver, Parotid Cells and Pancreatic Islets", Molecular and Cellular Biochemistry, 187, pp. 113-120, 1998.

Sener, et al., "Environmental Modulation of D-Fructose Insulinotropic Action", Acta Diabetol, 1998, 35, pp. 74-76.

Shimada, "Significance of 1,5-Anhydro-D-Glucitol in Diabetes Mellitus Management", Sangyo Igaku, 1994, 36(3), pp. 148-449.

Simon, et al., "Insulin and Proinsulin Secretion and Action", Israel J. Med. Sci., vol. 8, No. 6, Jun. 1972.

Walker-Bone, et al., "Natural Remedies in the Treatment of Osteoarthritis", Drugs and Aging, 2003, 20(7), pp. 517-526.

Wamelink, et al., "Detection of Transaldolase Deficiency by Quantification of Novel Seven-Carbon Chain carbohydrate Biomarkers in Urine", J. Inherit Metab Dis, (2007), 30, pp. 735-742.

Winnock, et al., "Correlation Between Gaba Release from Rat Islet beta-cells and their Metabolic State", Am. J. Physiol Endocrinol. Metab., 282: E937-E942, 2002.

Wood, et al., "Evidence for Insulin Involvement in Arginine- and Glucose-Induced Hypercalciuria in Rat", J. Nutr., 113, pp. 1561-1567, 1983.

Zhang, et al., "Dissimilar Effects of D-Mannoheptulose on the phosphorylation of alpha vs beta-D-glucose by either Hexokinase or Glucokinase", International Journal of Molecular Medicine, 14, pp. 107-112, 2004.

Andus, et al., "Imbalance of the Interleikin 1 System in Colonic Mucosa-Association with Intestinal Inflammation and Interleukin 1 Receptor Agonist Genotype 2", Gut, vol. 31, 1997, pp. 651-657.

Anonymous, "The Best Ever Guacamole—Again, Whole Foods Market", Jan. 18, 2013, Retrieved from the Internet: URL:http://www.wholefoodsmarket.com/blog/best-ever-guacamole-again, p. 3.

Apgar, et al., "Effect of feeding Various Levels of Bifidobacterium globosum A on the Performance, Gastrointestinal Measurements and Immunity of Weanling Pigs and on the Pelfromance and Carcass Measurements of Gorwing-Finishing Pigs", J. Animal Science, 1993, vol. 71, pp. 2173-2179.

Aranda, et al., "Analysis of Intestinal Lymphocytes in Mouse Colitis Medicated by Transfer of CD4+, CD45RB High T Cells in SCID Recipients", 1997, The American Assoc. of Immunologists.

Arany, et al., "The Effect of Carcinogens and Non-Carcinogens on Some Biochemical Features of the Mouse Lung Tissue", Arch. Toxicol., Suppl. 4, 73 (1980).

Asahara, et al., "Antimicrobial Activity of Intraurethrally Adminstered Probiotic Lactobacillus casei in a Murine Model of *Escherichia coli*Urinary Tract Infection", Antimicrobial Agents & Chemotherapy, 2001, 45(6): 1751-1760.

Barbara, et al., "A Role for Inflammation in Irritable Bowel Syndrome", Gut, 2002, 51 (Suppl I), pp. i41-i44.

Begbie, et al., "The Isolation of Some Heptoses, Heptuloses, Octuloses and Nonuloses from Pimula Officinalis JACQ", Carbohydrate Research, 1966, vol. 2, pp. 272-288.

Benno, et al., "Individual and Seasonal Variations in the Composition of Fecal Microflora of Beagle Dogs", Bifidobacteria Microflora, vol. 11, No. 2, pp. 69-76, 1992.

Biavati, et al., "Electrophoretic Patterns of Proteins in the Genus Bifidobacterium and Proposal of Four New Species", Journal Int. J. Syst. Bacteriol., vol. 32, pp. 358-373, 1982.

Bodmeier, "Capsule with Controlled Active Ingredient Release Comprises Active Ingredient Containing Filling, 2, Capsule Shell, Swelling Agent and Water-Insoluble Layer", BODM, May 18, 1999.

Botterweck, et al., "Intake of Butylated Hydroxyanisole and Butylated Hydroxytoluene and Stomach Cancer Risk: Results from Analyses in the Netherlands Cohort Study", Food and Chemical Toxicology, 38 (2000, 599-605.

Bouhnik, et al., "Effects of Bifidobacterium SP Fermented Milk Ingested with or without Inulin on Colonic Bifidobacteria and Enzymatic Activities in Healthy Humans", European Journal of Clinical Nutrition, 1996, 50, pp. 269-273.

Brandtzaeg, et al., "Immunopathology of Human Inflammatory Bowel Disease", Springer Seminars in Immunopathology, 1997, 18, pp, 555-589.

Bridigidi, et al., "Specific Detection of Bifidobacterium Strains in a Pharmaceutical Probiotic Product and in Human Feces by Polymerase Chain Reaction", System Appl. Microbiol., 23, 2000, 391-399.

Campieri, et al., "Reduction of Oxaluria after an Oral Course of Lactic Acid bacteria at High Concentration", Kidney International (2001) vol. 60, pp. 1097-1105.

Chadwick, et al., "Activation of the Mucosal Immune System in Irritable Bowel Syndrome", Gastroenterology, 2002, 122, pp. 1778-1783.

Charteris, et al., "Antibiotic Susceptibility of Potentially Probiotic Bifidobacterium Isolates from the Human Gastrointestinal Tract", Letters in Applied Microbiology, 1998, vol. 26, pp. 333-337.

Charteris, et al., "Development and Application of an in Vitro Methodology to Determine the Transit Tolerance of Potentially Probiotic *Lactobacillus* and *Bifidobacterium* Species in the Upper Human Gastrointestinal Tract", Journal of Applied Microbiology, 1998, vol. 84, pp. 759-768.

Charteris, et al., "Effect of Conjugated Bile Salts on Antibiotic Susceptibility of Bile Salt-Tolerant Lactobacillus and Bifidobacterium Isolates", Journal of Food Protection, vol. 63, No. 10, 2000, pp. 1369-1376.

Charteris, et al., "Selective Detection, Enumeration and Identification of Potentially Probiotic Lactobacillus and Bifidobacterium Species in Mixed Bacterial Populations", International Journal of Food Microbiology, 35, 1997, pp. 1-27.

Chauviere, et al., "Adhesion of Human Lactobacillus Acidophilus Strain LB to Human Enterocyte-like Caco-2 Cells", Journal of General Microbiology, 1992, vol. 138, pp. 1689-1696.

Chen, et al., "Action of 5-Thio-D-Glucose and Its 1-Phosphate with Hexokinase and Phosphoglucomutase", Arch. Biochem. Biophys. 169, pp. 392-396 (1975).

Chevalier, et al., "Detection of Bifidobacterium Species by Enzymatic Methods", Journal of Applied Bacteriology, 1990, vol. 68, pp. 619-624.

Chiricolo, et al., "Cell Adhesion Molecules CD11a and CD18 in Blood Monocytes in Old Age and the consequences for Immunological Dysfunction", Gerontology, 1995, 41(4), pp. 227-234.

Cicco, et al., "Inducible Production of Interleukin-6 by Human Polymorphonuclear Neutrophils: Role of Granulocyte-Macrophage Colony-Stimulating Factor and Tumor Necrosis Factor-Alpha", The American Society of Hematology, Blood, vol. 75, No. 10, May 15, 1990, pp. 2049-2052.

Collins, et al., "A Randomised Controlled Trial of a Probiotic Lactobacillus Strain in Healthy Adults: Assessment of its Delivery, Transit and Influence on Microbial Flora and Enteric Immunity", Microbial Ecology in Health and Disease, vol. 14, No. 2, Jun. 2002, pp. 81-89.

Collins, et al., "Selection of Probiotic Strains for Human Applications", Dairy Journal, 8, 1998, 487-490.

Cooke, et al., "Role of Estrogens in Adipocyte Development and Function", Exp. Biol. Med., 229:1127-35, 2004.

Mane, et al., "The Non-Competitive Inhibition of Brain Hexokinase by Glucose-6-Phosphate and Related compounds", Biol. Chem., 210, pp. 597-696 (1954).

Cruzen, et al., "Effects of Caloric Restriction on Cardiovascular Aging in Non-Human Primates and Humans", Clin. Geriatr. Med., vol. 25(4), pp. 733-743, Nov. 2009.

De Pergola, "The Adipose Tissue Metabolism: Role of Testosterone and Dehydroepiandrosterone", Int. J. Obesity, 24: S59-S63, 2000.

Dent, et al., "Lactobacillus animalis JCM5670", Database JCM Catalogue, Japan Collection of Microorganisms, 1986, XP002447035.

(56) References Cited

OTHER PUBLICATIONS

Donnelly, et al., "Differential Regulation of Il-1 Production in Human Monocytes by IFN-y and IL-4", The Journal of Immunology, vol. 145, pp. 569-575, No. 2, Jul. 15, 1990.

Dreau, et al., "Effects of 2-deoxy-D-glucose Adminstration on Immune Parameters in Mice", Immunopharmacology, vol. 39, Jun. 1, 1998, pp. 201-213.

Dunne, et al., "Probiotics: From Myth to Reality, Demonstration of Functionality in Animal Models of Disease and in Human Clinical Trials", Antonie Van Leeuwenhoek. Jul.-Nov. 1999;76(1-4):279-92.

Eisai, "Sustained-Release Solid Preparation of Zero Order Drug Releasing Profile Comprises Granules Obtainable by Coating Inner Core Containing Xanthine Deriv. Etc, with Film of Hardened Oil", EISA, Dec. 22, 1989.

Fajans, et al., "Stimulation of Insulin Release in the Dog by a Nonmetabolizable Amino Acid. Comparison with Leucine and Arginine", J. of Clinical Endocrinology and Metabolism, 33(1) 35-41, Jul. 1971.

Fontana, et al., "Long-term Calorie Restriction is Highly Effective in Reducing the Risk for Artherosclerosisin Humans", PNAS, vol. 101(17), pp. 6659-6663 (2004).

Freund, "Capsule Containing Useful Enteric Bacteria-includes Hydrophobic Layer Non-fluid at Room Temp Isolating Bacteria from Membrane, to prevent Moisture Penetration", Derwent Publ. Ltd. FREN, Aug. 5, 1986.

Gasche, et al., "IL-10 Secretion and Sensitivity in Normal Human Intestine and Infalmmatory Bowel Disease", Journal of Clinical Immunology, vol. 20, No. 5, 2000.

Gatrell, et al., "The Effects of Chocolate and Chocolate by-product Consumption on Wild and Domestic Animals", Chocolate in Health and Nutrition, Humana Press, 2013, pp. 135-141.

German, et al., "Glucose Sensing in Pancreatic Islet Beta Cells: The Key Role of Glucokinase and the Glycolytic Intermediates", Proc. Nat. Acad. Sci., 90, 1781-1785 (1993).

Gibson, et al., "Dietary Modulation of the Human Gut Microflora Using Probiotics", Journal of Nutrition, 1998, 80, suppl 2, S209-S212.

Gielkens, et al., "Effects of Hyperglycemia and Hyperinsulinemia on Satiety in Humans", Metabolism, vol. 47, No. 3, pp. 321-324, 1998.

Van Damme, et al., "The Proportion of Th 1 Cells, Which Prevail in Gut Mucosa, is Decreased in Inflammatory Bowel Syndrome", 2001, Blackwell Science Ltd. Clinical and Experimental Immunology, 125, pp. 383-390.

Vickers, et al., "Comparison of Fermentation of Selected Fructooligosaccharides and Other Fiber Substrates by canine Colonic Microflora", AJVR, vol. 62, No. 4, Apr. 2001.

Voet, et al., Biochemistry, John Wiley & Sons, Inc., pp. 1044-1045.

Wein, et al., "Analyzing a Bioterror Attack on the Food Supply: The Case of Botolinum Toxin in Milk", 2005, The National Academy of Sciences of the USA.

Weindruch, "The Retardation of Aging by Caloric Restriction", Toxicol. Pathol., 1996, 24:742.

Willott, et al., "Aging and Presbycusis: Effects on 2-Deoxy-D-Glucose Uptake in the Mouse Auditory Brain Stem in Quiet", Exp. Neurol., vol. 99(3), pp. 615-621.

Yaeshima, et al., "Bifidobacterium globosum, Subjective Synonym of Bifidobacterium pseudolongum, and Descrption of Bifidobacterium pseudolongum subsp. pseudolongum com nov. and Bifidobacterium psuedolongum subsp. globosum comb. nov.", Systematic and Applied Microbiology, 1992, vol. 15(3), pp. 380-385.

Yamamoto, et al., "Changes in Behavior and Gene Expression Induced by Caloric Restriction in C57BL/6 Mice", Physiological Genomics, vol. 39, No. 3, Sep. 8, 2009, pp. 227-235.

Yang, et al., "The Role of Voltage-Gated Calcium Channels in Pancreatic [beta]-Cell Physiology and Pathophysiology", Endocrine Reviews, vol. 27, No. 6, Oct. 1, 2006.

Yu, "Aging and Oxidative Stress: Modulation by Dietary Restriction", Free Radical Biology and Medicine, vol. 21, No. 5, pp. 651-668, 1996.

All Office Actions, U.S. Appl. No. 09/950,052 (now abandoned).

All Office Actions, U.S. Appl. No. 10/842,300.
All Office Actions, U.S. Appl. No. 11/313,198 (now abandoned).
All Office Actions, U.S. Appl. No. 11/313,199 (now abandoned).
All Office Actions, U.S. Appl. No. 12/012,317.
All Office Actions, U.S. Appl. No. 12/082,710.
All Office Actions, U.S. Appl. No. 12/168,400.
All Office Actions, U.S. Appl. No. 12/371,101.
All Office Actions, U.S. Appl. No. 12/371,266.
All Office Actions, U.S. Appl. No. 12/638,128.
All Office Actions, U.S. Appl. No. 12/716,533.
All Office Actions, U.S. Appl. No. 12/762,539.
All Office Actions, U.S. Appl. No. 12/939,594.
All Office Actions, U.S. Appl. No. 13/098,741.
All Office Actions, U.S. Appl. No. 13/098,756.
All Office Actions, U.S. Appl. No. 14/043,142.

Amendment in response to Nonfinal Office Action mailed Aug. 16, 2011 and issued in connection with U.S. Appl. No. 12/716,540 dated Nov. 15, 2011.

Amendment in response to Nonfinal Office Action mailed Jun. 10, 2011 and issued in connection with U.S. Appl. No. 12/638,101, Dated Sep. 2, 2011.

Amendment in response to Nonfinal Office Action mailed Jun. 7, 2011 and issued in connection with U.S. Appl. No. 12/716,518 dated Oct. 7, 2011.

Amendment in response to Nonfinal office Action mailed Jun. 9, 2011 and issued in connection with U.S. Appl. No. 12/716,562, dated Sep. 2, 2011.

Dorland's Pocket Medical Dictionary (24th ed.), W.B. Saunders Co. p. 15, 1989.

European Search Report Received in Connection with EP 04 81 5182, mailed on Jun. 13, 2008.

European Search Report Received in Connection with EP 04 81 5186, mailed on Jan. 7, 2013.

Final Office Action issued in connection with U.S. Appl. No. 12/638,101, mailed Dec. 30, 2011.

Final Office Action issued in connection with U.S. Appl. No. 12/716,518 mailed Jan. 4, 2012.

Final Office Action issued in connection with U.S. Appl. No. 12/716,540 mailed Jan. 10, 2012.

Final Office Action issued in connection with U.S. Appl. No. 12/716,562 mailed Dec. 29, 2011.

International Search Report for PCT/US2011/058861, dated Feb. 10, 2012.

International Search Report for PCT/US2012/035921, dated Jul. 10, 2012.

International Search Report for PCT/US2012/036035, dated Jul. 11, 2012.

International Search Report Received in Connection with PCT/US2004/043068, mailed on Sep. 25, 2007.

Nonfinal Office Action issued in connection with U.S. Appl. No. 12/638,101, mailed Jun. 10, 2011.

Nonfinal Office Action issued in connection with U.S. Appl. No. 12/716,540, mailed Aug. 16, 2011.

Nonfinal Office Action issued in connection with U.S. Appl. No. 12/716,562, mailed Jun. 9, 2011.

Nonfinal Office Action issued in connection with U.S. Appl. No. 12/716518 mailed Jun. 7, 2011.

Physician's Desk Reference, 1963 Edition, Medical Economics, Inc. Oradell, N.J., 1962, Product Identification Section, SEction Four, p. VIII and XI.

Supplemental Amendment in response to Nonfinal Office Action mailed Jun. 10, 201, and issued in connection with U.S. Appl. No. 12/638,101, dated Sep. 29, 2011.

LabScan XE User's Manual, Manual Version 1.2, A60-1010-862, Jan. 2003, 53 pp.

"Changing Times", The Kiplinger Magazine, vol. 31, No. 1, Jan 1977, pp. 39-40.

"Lactobacillus animalis genes for 16S-23S intergenic spacer region, 23S ribosomal RNA, strain", Database EMBL: JCM 5670, Jul. 9, 2004, XP002447038.

"Lactobacillus murinus genes for 16S-23S intergenic spacer regions, 23S ribosomal RNA, strain: JCM 1717", Database EMBL, Jul. 9, 2004, XP002447039.

(56) References Cited

OTHER PUBLICATIONS

"Nutrient Profiles for Dog Foods", Association of American Feed Control Officials Incorporated, pp. 110-119, 1994.
Alves-Filho, Drying Technology, 2002, vol. 20, No. 8, pp. 1541-1557, abstract.
Anand, et al., "Cytokines and Inflammatory Bowel Disease", Tropical Gastroenterology, 1999, 20(3), pp. 97-106.
Anderson, et al., Nutrition Reviews, vol. 61, No. 5, pp. S17-S26, May 2003.
Naaz, et al., "THe Soy Isoflavone Genistein Decreases Adipose Deposition in Mice", Endocrinology, 144 (8):3315-3320, 2003.
Novogrodsky, et al., "Lymphocyte Transformation Induced by Concanavalin A and its Reversion by methyl-alpha-D-mannopyranoside", Biochim. Biophys. Acta, 1971, 228, 579-583.
Obaldiston, et al., "Microflora of Alimentary Tract of Cats", American Journal of Veterinary Research, vol. 32, No. 9, Sep. 1971, pp. 1399-1405.
O'Callaghan, et al., "Differential Cytokine Response of Cells Derived from Different Lymphoid Compartments to Commensal and Pathogenic Bacteria", Gastroenterology, Apr. 2003, vol. 124, Issue 4, Supplement 1, p. A339.
O'Mahony, et al., "Probiotic Human Bacteria: Selection of a New Strain and Evaluation in Vitro and In Vivo", Gastroenterology, vol. 118, No. 4, Apr. 2000.
O'Mahony, et al., "Probiotic Impact on Microbial Flora, Inflammation and Tumour Development in IL-10 Knockout mice", Aliment Pharmacol Ther., 2001, 15, pp. 1219-1225.
Panwala, et al., "A Novel Model of Inflammatory Bowel Disease: Mice Deficient for the Multiple Drug Resistance Gene, mdria, Spontaneously Develop Colitis", The American Association of Immunologists, 1998. The Journal of Immunology, 1998, 161, pp. 5733-5744.
Park, et al., "Species Specific Oligonucleotide probes for the detection and identification of *Lactobacillus* isolated from mouse feces", Journal of Applied Microbiology, 2005, vol. 99, pp. 51-57, XP002447051.
Pawelec, et al., "T Cell Immunosenescence In Vitro and In Vivo", Exp. Gerontol, 1999, 34: 419-429.
Perlmann, et al., "Inhibition of Cytotoxicity of Lymphocytes by Concanavalin A in vitro", Science, 1970, 168:1112-1115.
Powrie, et al., "Inhibition of Th1 Responses Prevents Inflammatory Bowel Disease in Scid Mice Reconstituted with CD45Rbhi CD4+ T Cells", Immunity, vol. 1, pp. 553-562, Oct. 1994.
Purina, "Advancing Life Through Diet Restriction", The Purina Pet Institute Symposium, 2002.
Raonimalala, et al., "Action of Soluble Carbohydrates from Avocado Fruit on Utilization of Calcium in the Rat", Ann. Nutr Aliment, 34(4), 734-744, 1980.
Rastall, "Baceria in the Gut: Friends and Foes and How to Alter the Balance", The Journal of Nutrition, Waltham Intl Science Symposium: Nature, Nurture, and the Case for Nutrition (2004), pp. 2022S-2026S.
Reid, et al., "Prevention of Urinary Tract Infection in Rats with an Indigenous Lactobacillus Casei Strain", Infection and mmunity, 1985, 49(2), pp. 320-324.
Riquelme, et al., "Regulation of Carbohydrate Metabolism by 2,5-Anhydro-D-Mannitol", PNAS, 80, pp. 4301-4305 (1983).
Rodtong, et al., NCBI Genbank Accession No. AF080100, NCBI Genbank (1998).
Roe, et al., "Further Studies of the Physiological Availability of Heptoses", J. Biol. Chem., 121:37-43, 1937.
Rogler, et al., "Cytokines in Inflammatory Bowel Disease", World Journal of Surgery, vol. 22, 1998, pp. 382-389 KP002296948.
Rowland, et al., "Physiological and Behavioral Responses to Glucoprivation in the Golden Hamster", Physiology and Behavior, vol. 30, No. 5, May 1, 1983, pp. 747-747.
Ruscetti, et al., "Release of Colony-Stimulating Activity from Thymus-Derived Lymphocytes", J Clin Invest. 1975;55 (3):520-527.

Sayegh, et al., "Impact of Hormone Replacement Therapy on the Body Mass and Fat Compositions of Menopausal Women: A Cross-Sectional Study", Menopause, 6:312-315, 1999.
Scardovi, et al., "Deoxyribonucleic Acid Homology Relationships Among Species of the Genus Bifidobacterium", Int. J. Syst. Bacteriol., vol. 21, pp. 276-294, 197.
Scardovi, "Irregular Nonsporing Gram-Positive Rods", *Genus Bifidobacterium Orla Jensen*, 1924, 472.
Schmitt, et al., "The Immunostimulatory Function of IL-12 in T-Helper Cell Development and its Regulation by TGF-B, IFN-y and IL-4", Chem. Immunet Basel Karger, 1997, vol. 68, pp. 70-85.
Scrimshaw, et al., "Interactions of Nutrition and Infection", Am. J. Med. Sci., 1959, 237: 367-403.
Shanahan, et al., "Genes, Bacteria and T Cells: Ingredients for Inflammatory Bowel Disease", Selected Summaries, Gastroenterology, 1998, 115, pp. 1595-1600.
Shanahan, "The Intestinal Immune System", Physiology of the Gastrointestinal Tract, 3rd. ed., 1994.
Silva De Ruiz, et al., "Effect of Lactobacilli and Antibiotics on *E. coli* Urinary Infections in Mice", Biol. Pharm. Bull., 1996, 19(1): 88-93.
Simon, et al., "Metabolism of Mannoheptulose in the Rat. I. Diabetogenic Action", Arch. Biochem. Biophys., 69, pp. 592-601 (1957).
Simpson, et al., "Genomic Diversity and Relatedness of Bifidobacteria isolated from a Porcine Cecum", Journal of Bacteriology, Apr. 2003, vol. 185, pp. 2571-2581.
Snow Brand Milk Products, "Enteric Capsules—comprising Core Contaiing Drug etc. AndCoating of Hardened Oil of M. Pt. Higher than Body Temp and Disintegrated by Lipase in Intestine", SNOW, Mar. 31, 1986.
Sols, et al., "Substrate Specificity of Brain Hexokinase", Biol. Chem. 210, pp. 581-595 (1954).
Soudeyns, et al., "The Moving Target: Mechanisms of HIV Persistance During Primary Infection", Immunology Today, Oct. 1999.
SS Pharmaceutical KK, "Tablets Containing Double-Coated Granules-Obtained by Coating with Insol. Polymer, Enteric Polymer and/or Waces, Then Further Coating with Water or Acid-Soluble Polymer", SSSE, Aug. 18, 1988.
Stallmach, et al., "Induction and Modulation of Gastrointestinal Inflammation", Trends Immunology Today, Oct. 1998, vol. 19, No. 10, pp. 438-441.
Strober, et al., "Reciprocal IFN-Gamma and TFG-Beta Responses Regulate the Occurrence of Mucosal Inflammation", Immunol. Today, Feb. 18, 1997, 2, pp. 61-64.
Sung, et al., "The Sphincter of Oddi is a Boundary for Bacterial Colonization in the Feline Biliary Tract", Microbial Ecology in Health and Disease, 1990, vol. 3, pp. 199-207.
Sunvold, et al., "Dietary Fiber for Dogs: IV. In Vitro Fermentation of Selected Fiber Sources by Dog Fecal Inoculum and In Vivo Digestion and Metabolism of Fiber-Supplemented Diets", J. Anim. Sci., vol. 73, 1995, 1099-1109.
Takeda Chemical Ind KK, "Dry Coated Tablet—Comprises Core Tablets Containing Enzyme Prepn in Enteric Films Within Outer Shell", Take, May 10, 1982.
Tomomatsu, "Health Effects of Oligosaccharides", 1994, Food Technology, 48, pp. 61-65.
Trovatelli, et al., "Presence of Bifidobacteria in the Rumen of Calves Fed Different Rations", Appl. Environ. Microbiol., 1976, vol. 32(6), pp. 470-473.
Valente, et al., "Immunologic Function in the Elderly After Injury—The Neutrophil and Innate Immunity", The Journal of Trauma Injury, Infection and Critical Care, vol. 67, No. 5, pp. 968-974, Nov. 2009.
Miller, et al., "2-Deoxy-D-Glucose-Induced Metabolic Stress Enhances Resistance to Listeria monocytogenes Infection in Mice", Physiology & Behavior, vol. 65., No. 3, pp. 535-543, 1998, 1998, 535-543.
Miller, et al., "The Metabolic Stressor 2-Deoxy-D-Glucose (2-DG) Enhances LPS-Stimulated Cytokine Production in Mice", Brain, Behavior, and Immunity, 1993, vol. 7, pp. 317-325, 1993, 317-325.
Ogawa, Journal of Japan Mibyou System Association, 2004, vol. 10, No. 1, p. 140-142 (with machine translation), 2004, 140-142.

(56) References Cited

OTHER PUBLICATIONS

Takayanagi, J. Nippon Med. Sch., 2003, vol. 70, No. 1, p. 71 (with machine translation), 2003, 71.
Goldrosen, et al., "Impaired Lymphocyte Blastogenic Response in Patients with Colon Adenocarcinoma: Effects of Disease and Age", Journal of Surgical Oncology, 9:229-234, 1977.
Golkar, et al., "Apigenin Inhibits Pancreatic Cancel Cell Proliferation via Down-Regulation of the GLUT-1 Glucose Transporter", Gastroenterology, vol. 130, No. 4, Jul. 22, 2006.
Grajales-Lagunes, et al., "Stability and Sensory Quality of Spray Dried Avocado Paste", Drying Technology, Vo. 17, No. 1&2, 1999, pp. 317-326.
Greetham, et al., "Bacteriology of the labrador dog gut: A cultural and genotype approach", J. Appl. Microbiol., 93:640-646, 2002.
Groux, et al., "Regulatory T Cells and Inflammatory Bowel Disease", Viewpoint Immunology Today, Oct. 1999.
Hammarstrom, et al., "Mitogenic Leukoagglutinin from Phaseolus vulgaris Binds to a Pentasaccharide Unit in N-acetyllactosamine-type Glycoprotein Glycans", Proc. Natl. Acad. Sci. USA, 79, 1611-1615 (1982).
Hemme, et al., "Lactobacillus murinus JCM1717", Database JCM Catalogue, Japan Collection of Microorganisms, 1982, XP002447036.
Hershkovitz, et al., "Ethylene regulation of Avocado Ripening Differs Between Seeded and Seedless Fruit", Postharvest Biology and Technology, vol. 56, No. 2, May 1, 2010, pp. 138-146.
Hildesheim, et al., "Simultaneous Measurement of Several Cytokines Using Small Volumes of Biospecimens", Cancer Epidemiology, Biomarkers & Prevention, vol. IK1, pp. 1477-1484, Nov. 2002, abstract.
Hoffman, et al., "Diabetogenic Action of 5-Thio-D-glucopyranose in Rats", Biochemistry, vol. 7, pp. 4479-4483 (1968).
Hommes, et al., "Anti- and Proinflammatory Cytokines in the Pathogenesis of Tissue Damage in Crohn's Disease", 2000 Lippincott Williams and Wilkins, pp. 1363-1950.
Isolauri, et al., "Probiotics: A Role in the Treatment of Intestinal Infection and Inflammation?", Gut, 2002, 50 (Suppl III), pp. iii54-iii59.
Iwasaki, et al., "Unique Functions of CD11b+, CD8a+ and Double Negative Peyer's Patch Dendritic Cells", 2001, The American Association of Immunologists.
Jay, et al., "Metabolic Stability of 3-O-Methyl-D-Glucose in Brain and Other Tissues", J. Neurochem., 55, pp. 989-1000 (1990).
Johnston, "Small Intestinal Bacterial Overgrowth", The Veterinary Clinics of North America, Small Animal Practice, Mar. 1999, vol. 29, No. 2, Mar. 1999, pp. 523-550.
Kalani, et al., "Effects of Caloric Restriction and Exercise on Age-Related, Chronic Inflammation Assessed by C-Reactive Protein and Interleukin-6", J. Gerontol. A. Bio. Sci. Med. Sci., vol. 61(3), pp. 211-217 (2006).
Kaufman, et al., "Identification and Quantification of Bifidobacterium Species Isolated from Food with Genus-Specific 16S rRNA-Targeted Probes by Colony Hybridization and PCR", Appl. Environ. Microbiol., Apr. 1997, vol. 63, pp. 1268-1273.
Koizumi, et al., "Influences of Dietary Restriction and Age on Liver Enzyme Activities and Lipid Peroxidation in Mice", J. Nutr., 117: 361-367, 1987.
Kok, et al. , "Specific Detection and Analysis of a Probiotic Bifidobacterium Strain in Intact Feces", Applied and Environmental Microbiology, 1996, vol. 62, pp. 3668-3672.
Kudo, et al., "An Electron Microscopic Study on Bifidobacterium Pseudolongum SS-24 with Extracellular Material and Naked Bifidobacterium Thermophilum SS-19", AJAS, vol. 2, No. 3, pp. 444-445, 1989.
Kyoto, "Sustains-Release Formulation which Floats in Stomach-Comprises Core of Fats and Oils, Coated with Drug Containing Layer of e.g., Agar", KYOT, Jul. 10, 1987.
La Forge, "D-Mannoketoheptose, A New Sugar from the Avocado", J. Biol. Chem. 28:511-22, 1917.
Lab Prod Ethiques Ethypharm, "Coated Microgranules Containing a Gastric Proton Pump Inhibitor with Two Hydrophobic Materials, Free from Alkali and any Ionic Surfactant", Derwent Publications Ltd., Ethi., May 21, 1999.
Lakatos, "Immunology of Inflammatory Bowel Diseases", Acta Physiological Hungarica, vol. 87 (4), pp. 355-372, 2000.
Leblond-Bourget, et al., "16S rRNA and 16S to 23S Internal Transcribed Spacer Sequence Analysis Reveal Inter- and Intraspecific Bifidobacterium Phylogeny", International Journal of Systemic Bacteriology, vol. 6, No. 1, Jan. 1996, pp. 102-111.
Leclercq-Meyer, et al., "Effects of D-mannoheptulose and Its Hexaacetate Ester on Hormonal Secretion From The Perfused Pancreas", International Journal of Molecular Medicine, 2000, vol. 6, pp. 143-152.
Lee, "Medicinal Plant Composition Suitable for Each Blood Type", WPI/Thomson, vol. 2004, No. 46, Mar. 22, 2004.
Libby, "Inflammatory mechanisms: the molecular basis of inflammation and disease", Nutr. Rev., Dec 2007, 65 (12 Pt. 2): S140-6.
Mamula, et al., Gastrointestinal Tract Infections—Chapter 11. 2004, pp. 79-89.
Marteau, et al., "Potential of Using Lactic Acid Bacteria for Therapy and Immunomudulation in Man", FEMS Microbiology Reviews, 12, 1993, pp. 207-220.
Masoro, "Overview of Caloric Restriction and Aging", Mech. Aging Dev., vol. 126, pp. 913-922 (2005).
Massi, et al., NCBI Genbank Accession No. AB102854, NCBI Genbank (1994).
Mattarelli, et al., "Characterization of the plasmid pVS809 from Bifidobacterium globosum", Microbiologica, 1994, vol. 17, pp. 327-331.
Mattson, et al., "Beneficial Effects of Intermittent Fasting and Caloric Restriction on the Cardiovascular and Cerebrovascular Systems", J. Nutr, Biol. 16, 3:129-137, 2005.
McCarthy, et al., "Double Blind Placebo Controlled Trial of Two Probiotic Strains in Interleukin", Gastroenterology, vol. 122, No. 4, suppl., 1, pp. A389-A390, DDW Meeting Abstract, Nr. T962.
McCracken, et al., "Probiotics and the Immune System", in G. W. Tannock (ed.), Probiotics, a critical review. Horizon Scientific Press, Norfolk, United Kingdom, 1999, p. 85-112.
McGee, et al., "A Synergistic Relationship Between TNF-alpha, IL-1B, and TGF-B1 on IL-6 Secretion by the IEC-6 Intertinal Epithelial Cell Line", Immunology, 1995, 86, pp. 6-11.
McKay, et al., "Review Article: In Vitro Models in Inflammatory Bowel Disease", Aliment Pharmacol. Ther., 1997, 11 (suppl. 3), pp. 70-80.
Mentula, et al., "Comparison Between Cultured Small-Intestinal and Fecal Microbiotas in Beagle Dogs", Applied and Environmental Microbiology, Aug. 2005, vol. 71, No. 8, p. 4169-4175.
Meyer, et al., "Long-Term Caloric Restriction Ameliorates the Decline in Diastolic Function in Humans", J. Am. College of Cardiology, vol. 47(2), pp. 398-402 (2006).
Mitsuoka, et al., "Ecology of the Bifidobacteria.", The American Journal of Clinical Nutrition, Nov. 1977, vol. 30, pp. 1799-1810.
Mohamed, et al., "Effect of Long-Term Ovariectomy and Estrogen Replacement on the Expression of Estrogen Receptor Gene in Female Rats", Eur. J. Endocrinol., 15, 142:307-14, 2000.
Molteleone, et al., "Manipulation of Cytokines in the Management of Patients with Inflammatory Bowel Disease", Ann. Med, Nov. 2000, 32(8), pp. 552-560.
Morishita Jintan KK, "Capsule Preparation for Enteral Adminstration of Unsaturated Fatty Acids", Derwent Publications Ltd, MORI, Oct. 30, 1997.
Moustafa, et al., "Effects of aging and antioxidants on glucose transport in rat adipocytes", Gerontology, 1995, 41 (6)301-7.
"A Balanced Diet", Waltham Book of Dog and Cat Nutrition, Ed. ATB, Edney, Chapter by A. Rainbird, pp. 57-74, Pergamon Press, Oxford, 1988.
"Kidney Stones in Adults (http://kidney.niddk.nih.gov, pp. 1-14).", cited by USPTO in connection with U.S. Appl. No. 11/012,570 on Dec. 12, 2005.
"Mice and Rats", (www.petswarehouse.com, pp. 1-5), cited by USPTO in connection with U.S. Appl. No. 11/012,570 on Dec. 12, 2005.

(56) References Cited

OTHER PUBLICATIONS

"Probiotic Basics", (www.usprobiotics.org.basics/, p. 1-12), cited by USPTO in connection with U.S. Appl. No. 11/012,570 on Dec. 12, 2005.

"Urinary Tract Infections in Adults", (http://kidney.niddk.nih.gov, pp. 1-11), cited by USPTO in connection with U.S. Appl. No. 11/012,570 on Dec. 12, 2005.

Arai, et al., "Cytokines: Coordinates of Immune and Inflammatory Responses", Annu. Rev. Biochem., 1990, 59: 783-836.

Barrows, et al., "Diet and Nutrition", Walleye Culture Manual, R. C. Summerfelt, editor, NCRAC Culture Series 101, North Central Regional Aquaculture Center Publications Office, Iowa State University, Ames, First Edition, 1996.

Collins, "Probiotics and Man—The Host Microbe Interface", Abstracts, Gastroenterology, vol. 116, No. 4, Apr. 1999.

Favier, et al., "Fecal B-D-Galactosidase Production and Bifidobacteria are Decreased in Crohn's Disease", Digestive Diseases and Sciences, vol. 42, No. 4, Apr. 1997, pp. 817-822.

Fujisawa, "Long-Acting Oral Prepn.—comprises Rapidly Soluble Inner Layer and Sustained Release Outer Layer, Both Layers Containing Principal Agent, which is Coronary or Peripheral Vasodilator", FUJI, Sep. 20, 1991.

Hillsvet, "Hill's Presciption Diet, A New Way to Define Pet Obesity", Internet Article, 2010, http://www.hillsvet.com/conference-documents/Weight_ManagementfTherapeutic?Weight_Reduction_Program/BFI_Backgrounder_pdf.

McBrearty, et al., "Probiotic Bifidobacteria and Their Identification Using Molecular Genetic Techniques", Teagasc, Dairy Products Research Centre, Moorepark, Fermoy, Co., Cork, Ireland, Department of Microbiology, University College, Cork Ireland, In, J. Buttriss and M. Saltmarsh (ed), 2000, p. 97-107, Royal Society of Chemistry, Cambridge, United Kingdom.

Medaglini, et al., "Mucosal and Systemic Immune Responses to Recombinant Protein Expressed on the Surface of the Oral Commensal Bacterim Streptococcus gordonil after Oral Colonization", Proc. Nat. Acad. Sci. USA, vol. 92, pp. 3868-6872, Jul. 1995, Medical Sciences.

Morishita Jintan KK, "Yogurt for Supply Physiologically Important Intestinal Bacteria—Contains Bacteria contained in Capsule Havingn Inner Layer Made of Digestible Substance and Outer Layer Dissolving in Intesting", MORI, Mar. 10, 1995.

Murphy, et al., "Evaluation and Characterisation of Probiotic Therapy in the CD45RB Transfer Model of Colitis", AGA Abstracts, Gastroenterology, vol. 116, No. 4, Apr. 1999.

O'Callaghan, et al., "Human Cytokine Production by Mesenteric Lymph Node Cells in Response to Probiotic and Pathogenic Bacteria", Gastroenterology, vol. 122, No. 4, Suppl. 1., pp. A -151 DDW Meeting Abstract No. S1043, Apr. 2002, XP09036734.

O'Halloran, et al., "Adhesion of Potential Probiotic Bacteria to Human Epithelial Cell Lines", Departments of Microbiology and Medicine, University College, Mercy Hospital, Cork, Ireland, Dept of Surgery, Mercy Hospital Cork, Ireland, 1998.

O'Mahony, et al., "Probiotic Bacteria and Pathogenic Bacteria Elicit Differential Cytokine Responses from Dendritic ells", Gastroenterology, 120(5) 1625, Suppl., Apr. 1, 2001, Xp-001097379.

O'Mahony, et al., "Probiotic Bacteria and the Human Immune System", Proceedings of the British Nutrition Foundation/Royal Society of Chemistry (Food Chemistry Group) "Functional Foods '99—Claims and Evidence". BNF (London), 2000, pp. 63-70.

Schrek, et al., "Characterizatoin of the B Lymphocyte Response to Pokeweed Mitogen", Annals of Clinical and Laboratory Science, 1982, vol. 12, Issue 6, pp. 455-462.

Stagg, et al., "The Dendritic Cell: Its Role in Intestinal Inflammation and Relationship with Gut Bacteria", Gut, 2003: 52: 1522-1529.

Tesfay, et al., "Anti-Oxidant Levels in Various Tissues During the Maturation of "Hass" Avocado", Journal of Horticultural Science and Biotechnology, (2010) 85(2): 106-112.

Seikagaku jiten (third edition), Tokyo Kagaku Dojin Publishing Co., Inc., 1998, pp. 657-658.

* cited by examiner

METHOD FOR DECREASING INFLAMMATION AND STRESS IN A MAMMAL

CROSS-REFERENCE TO RELATED APPLICATIONS

This application claims the benefit of U.S. Provisional Application No. 60/898,788, filed Feb. 1, 2007, and is a continuation-in-part application of U.S. application Ser No. 10/842,301, filed May. 10, 2004, patented on Feb. 23, 2010, as U.S. Pat. No. 7,666,459.

FIELD OF THE INVENTION

The present invention is directed to a method for decreasing inflammation and stress in a mammal comprising; administration to a mammal a composition comprising a glucose anti-metabolite; and wherein said composition comprises amounts of the glucose anti-metabolite sufficient to lower a level of a C-reactive protein in the blood of the mammal subsequent to administration of the glucose anti-metabolite.

BACKGROUND OF THE INVENTION

Studies have indicated that restriction of caloric intake by food deprivation slows down certain undesirable cellular processes in laboratory animals, many associated with aging and age-related diseases.

C-reactive protein (abbreviated as CRP) is one kind of acute phase protein, and although its blood level rapidly increases on inflammatory diseases or the like accompanying the disorganization, it is present in healthy mammal blood.

The inflammatory response plays an important role in the onset, development and evolution of stress, cardiac ischemia, and arthritic changes. Elevated serum levels of C-reactive protein (CRP) are non-specific but sensitive markers of the acute inflammatory response. C-reactive protein is an acute phase reactant protein. However, C-reactive protein levels can increase up to 100 or even 500 times during acute inflammation. This staggering response is mainly regulated by proinflammatory cytokines, in particular interleukin-6, and is largely unaffected by anti-inflammatory drugs and hormones. This suggests that the proinflammatory effects of C-reactive protein may contribute to the adverse outcome associated with higher levels of this acute phase reactant protein.

Additionally, due to its ligand binding properties, C-reactive protein plays a part in the innate immunity (opsonization) and in the removal of membrane and nuclear material from necrotic cells. C-reactive protein can also bind to complement factor Clq and factor H and activate the classic pathway of complement activation. C-reactive protein is present in atherosclerotic plaques but not in the normal vessel wall where often co-localize with the terminal complement complex. C-reactive protein can also induce tissue factor expression by monocytes.

There still exists a need for a method for decreasing inflammation and stress in a mammal resulting in enhancement of quality of life of a mammal, increase the length of the lifespan of a mammal, and providing for a healthier mammal.

It is therefore an object of the present invention to provide a method for decreasing inflammation and stress in a mammal including a human and/or a companion animal comprising; administration to a mammal a composition comprising a glucose anti-metabolite, avocado, avocado extract or mannoheptulose; and wherein the composition comprises amounts of the glucose anti-metabolite, avocado extract, avocado or mannoheptulose sufficient to lower a level of a C-reactive protein in the blood of the mammal subsequent to administration of the glucose anti-metabolite, avocado extract, avocado or mannoheptulose.

SUMMARY OF THE INVENTION

The present invention is directed to a method for decreasing inflammation and stress in a mammal comprising; administration to a mammal a composition comprising a glucose anti-metabolite; and wherein the composition comprises amounts of the glucose anti-metabolite sufficient to lower a level of a C-reactive protein in the blood of the mammal subsequent to administration of the glucose anti-metabolite.

The present invention further relates to a method for decreasing inflammation and stress in a mammal comprising; administration to a mammal a composition comprising an avocado; and wherein the composition comprises amounts of the avocado sufficient to lower a level of a C-reactive protein in the blood of the mammal subsequent to administration of the avocado.

The present invention further relates to a method for decreasing inflammation and stress in a mammal comprising; administration to a mammal a composition comprising an avocado extract; and wherein the composition comprises amounts of the avocado extract sufficient to lower a level of a C-reactive protein in the blood of the mammal subsequent to administration of the avocado extract.

The present invention further relates to a method for decreasing inflammation and stress in a mammal comprising; administration to a mammal a composition comprising mannoheptulose; and wherein the composition comprises amounts of the mannoheptulose sufficient to lower a level of a C-reactive protein in the blood of the mammal subsequent to administration of the mannoheptulose.

DETAILED DESCRIPTION OF THE INVENTION

The method for the present invention comprises decreasing inflammation and stress in a mammal comprising; administration to a mammal a composition comprising a glucose anti-metabolite; and wherein the composition comprises amounts of the glucose anti-metabolite sufficient to lower a level of a C-reactive protein in the blood of the mammal subsequent to administration of the glucose anti-metabolite.

These and other limitations of the compositions and methods of the present invention, as well as many of the optional ingredients suitable for use herein, are described in detail hereinafter.

As used herein, the term "adapted for use" means that the composition described can meet the American Association of Feed Control Officials (AAFCO) safety requirements for providing animal food products for an animal as may be amended from time to time.

As used herein, the term "companion animal" means an animal preferably including (for example) dogs, cats, kitten, puppy, senior dog, senior cat, adult dog, adult cat, horses, cows, pigs, rabbits, guinea pig, hamster, gerbil, ferret, horses, zoo mammals, fish, birds and the like. Dogs, cats, kitten, puppy, senior dog, senior cat, adult dog, adult cat are particularly preferred.

As used herein, the term "composition" means a composition that can be administered to a human that is orally ingested by the human, bars, pills, capsules, administered to companion animal that is orally ingested by a companion animal, supplements for a companion animal, pet food, dog food, cat food, treats, biscuits, raw hide, treats, chews, fillers, gravy, sauce, beverage, supplemental water, and combinations thereof. The composition can be wet, moist, and/or dry.

The term "complete and nutritionally balanced" as used herein, unless otherwise specified, refers to a composition having all known required nutrients in proper amounts and proportions based upon the recommendation of recognized authorities in the field of animal nutrition.

As used herein, the term "mammal" includes humans and/or companion animals.

All percentages, parts and ratios as used herein are by weight of the total composition, unless otherwise specified. All such weights as they pertain to listed ingredients are based on the active level and, therefore do not include solvents or by-products that may be included in commercially available materials, unless otherwise specified.

The composition and methods of the present invention can comprise, consist of, or consist essentially of, the essential elements and limitations of the invention described herein, as well as any additional or optional ingredients, components, or limitations described herein or otherwise useful in compositions intended for mammal consumption.

Method

The present invention is a method for decreasing inflammation and stress in a mammal. The method comprises administration to a mammal a composition comprising a glucose anti-metabolite or a avocado or mannoheptulose or avocado extract; and wherein the composition comprises amounts of the glucose anti-metabolite or avocado or avocado extract or mannoheptulose sufficient to lower a level of a C-reactive protein in the blood of the mammal subsequent to administration of the glucose anti-metabolite or a avocado or avocado extract or mannoheptulose.

Composition Form

The compositions are adapted for use by mammals. The composition of the present invention is preferably administered to decreasing inflammation and stress by lowering the level of C-reactive protein in the blood of a mammal. The composition of the present invention can be a moist composition (i.e. those having a total moisture content of from about 16% to 50%, by weight of the product), and/or a wet composition (i.e. those having a total moisture content of greater than 50%, by weight of the product), and/or dry composition (i.e. those having a total moisture content of from about 0% to about 16%, by weight of the product). Unless otherwise described herein, wet composition, moist composition and/or dry composition are not limited by their composition or method of preparation.

The composition herein can be complete and nutritionally balanced. A complete and nutritionally balanced animal food composition may be compounded to be fed as the sole ration and is capable of maintaining the life and/or promote reproduction without any additional substance being consumed, except for water.

The composition and components of the present invention are selected for consumption by an animal and are not intended for consumption by humans. Non-limiting examples of compositions include supplements for an animal, pet food, dog food, cat food, treats, biscuits, raw hide, treats, chews, fillers gravy, sauce, beverage, supplemental water, and combinations thereof.

Additionally, administration in accordance with the present invention may be continuous or intermittent, depending, for example, upon the recipient's physiological condition, whether the purpose of the administration is therapeutic or prophylactic, and other factors known to skilled practitioners.

Glucose Anti-Abolite

The method of the present invention comprise administering to a mammal a composition that can comprise a glucose anti-metabolite. The glucose anti-metabolites affects the level of CRP present in the blood of a mammal by decreasing inflammation and therefore resulting in decreased CRP levels subsequent to a mammal ingesting a composition comprising glucose anti-metabolites.

The level of C-reactive protein in the blood subsequent to administration of a composition comprising a glucose anti-metabolite is from about 0 mg/L to about 100 mg/L, from about 0.1 mg/L to about 60 mg/L, from about 0.2 mg/L to about 40 mg/L, from about 0.3 mg/L to about 20 mg/L.

Nonlimiting examples of glucose anti-metabolites which are useful herein include 2-deoxy-D-glucose, 5-thio-D-glucose, 3-O-methylglucose, anhydrosugars including 1,5-anhydro-D-glucitol, 2,5-anhydro-D-glucitol, and 2,5-anhydro-D-mannitol, and mannoheptulose. Mannoheptulose is preferred for use herein.

The dose of glucose anti-metabolites given to a mammal, on a daily basis, is from about 0.1 mg/kg to about 1000 mg/kg, from about 2 mg/kg to about 100 mg/kg, from about 2 mg/kg to about 10 mg/kg, wherein (as will be commonly understood in the art) the "mg" refers to level of the component and the "kg" refers to kilograms of the mammal or from about 0.0001 gram to about 1 gram of glucose anti-metabolites per kilogram of the mammal. When glucose anti-metabolites is present in a composition, the glucose anti-metabolites is less than about 5%, or less than about 2%, or from about 0.0001% to about 0.5% of the glucose anti-metabolites, all by weight of the composition. The level of component may be determined by one of ordinary skill in the art based on a variety of factors, for example, the form of the pet food composition (e.g., whether a dry composition, moist composition, wet composition, or supplement, or any other form or mixture thereof). The ordinarily skilled artisan will be able to utilize the preferred optimal doses, and use these to determine the optimal level of component within a given pet food composition.

When the glucose anti-metabolite is mannoheptulose the dose of mannoheptulose given to a mammal, on a daily basis, is from about 0.1 mg/kg to about 1000 mg/kg, from about 1 mg/kg to about 100 mg/kg, from about 2 mg/kg to about 5 mg/kg, wherein (as will be commonly understood in the art) the "mg" refers to level of the mannoheptulose and the "kg" refers to kilograms of the mammal or from about 0.0001 gram to about 1 gram of mannoheptulose per kilogram of the mammal. When mannoheptulose is present in a composition, the mannoheptulose is less than about 5%, or less than about 2%, or from about 0.0001% to about 0.5% of the mannoheptulose, all by weight of the composition.

The level of C-reactive protein in the blood subsequent to administration of a composition comprising a mannoheptulose is from about 0 mg/L to about 100 mg/L, from about 0.1 mg/L to about 60 mg/L, from about 0.2 mg/L to about 40 mg/L, from about 0.3 mg/L to about 20 mg/L.

Avocado

The method of the present invention comprises administering to a mammal a composition that can comprise avocado. The avocado affects the level of CRP present in the blood of a mammal by decreasing inflammation and stress and therefore resulting in decreased CRP levels subsequent to a mammal ingesting a composition comprising avocado.

The level of C-reactive protein in the blood subsequent to administration of a composition comprising an avocado is from about 0 mg/L to about 100 mg/L, from about 0.1 mg/L to about 60 mg/L, from about 0.2 mg/L to about 40 mg/L, from about 0.3 mg/L to about 20 mg/L.

An avocado (also commonly referred to as alligator pear, aguacate, or palta) contains unusually enriched sources of mannoheptulose, as well as related sugars and other carbohydrates. Avocado is a sub-tropical evergreen tree fruit, growing most successfully in areas of California, Florida, Hawaii, Guatemala, Mexico, the West Indies, South Africa, and Asia.

Nonlimiting examples of species of avocado that can be used in the present invention include, for example, Persea Americana and Persea nubigena, including all cultivars within these illustrative species. Cultivars may include 'Anaheim,' 'Bacon,' 'Creamhart,' 'Duke,' 'Fuerte,' 'Ganter,' 'Gwen,' 'Hass,' 'Jim,' 'Lula,' 'Lyon,' 'Mexicola,' 'Mexicola Grande,' 'Murrieta Green,' 'Nabal,' 'Pinkerton,' 'Queen,' 'Puebla,' 'Reed,' 'Rincon,' 'Ryan,' 'Spinks,' 'Topa Topa,' 'Whitsell,' 'Wurtz,' and 'Zutano.' The fruit of the avocado is particularly preferred for use herein, which may contain the pit or wherein the pit is removed or at least partially removed. Fruit from Persea Americana is particularly preferred for use herein, as well as fruit from cultivars which produce larger fruits (e.g., about 12 ounces or more when the fruit is mature), such as Anaheim, Creamhart, Fuerte, Hass, Lula, Lyon, Murrieta Green, Nabal, Queen, Puebla, Reed, Ryan, and Spinks.

The dose of avocado given to a mammal, on a daily basis, is from about 100 mg/kg to about 200 g/kg, from about 200 mg/kg to about 20 g/kg, from about 400 mg/kg to about 10 g/kg, wherein (as will be commonly understood in the art) the "mg" or "g" refers to level of avocado and the "kg" refers to kilograms of the mammal or from about 0.001 gram to about 200 gram of avocado per kilogram of the mammal. When avocado is present in a composition, the avocado is less than about 50%, or less than about 25%, or from about 0.0001% to about 5% of the avocado, all by weight of the composition. The level of avocado may be determined by one of ordinary skill in the art based on a variety of factors, for example, the form of the composition (e.g., whether a dry composition, moist composition, wet composition, or supplement, or any other form or mixture thereof). The ordinarily skilled artisan will be able to utilize the preferred optimal doses, and use these to determine the optimal level of component within a given composition.

Advantageously, mannoheptulose or any other component may be present in the recited compositions as a component of plant matter such as avocado, or other enriched source of mannoheptulose such as alfalfa, fig, or primrose. The plant matter may include the fruit, seed (or pit), branches, leaves, or any other portion of the relevant plant or combination thereof. Additionally, plant matter from alfalfa, fig, or primrose is also reported to provide relatively high levels of mannoheptulose. Alfalfa is also referred to as Medicago sativa. Fig, or Ficus carica (including Cluster fig or Sycamore fig, for example) may also be used, as well as primrose or Primula officinalis.

The mannoheptulose or any other component can be extracted from the plant matter and or avocado to form a plant extract or component extract or avocado extract and then utilized in the composition of the present invention.

When an extract of plant matter is utilized in a composition herein, the component will be present from about 1% to about 99% of the component extract, from about 5% to about 75% of the component extract, from about 10% to about 50% of the component extract, all by weight of the extract.

When an avocado extract is utilized in a composition herein, the component will be present from about 1% to about 99% of the component extract, from about 5% to about 75% of the component extract, from about 10% to about 50% of the component extract, all by weight of the extract.

When an extract of plant matter is mannoheptulose and then utilized in a composition herein, the mannoheptulose will be present from about 1% to about 99% of mannoheptulose, from about 5% to about 75% of the mannoheptulose, from about 10% to about 50% of the mannoheptulose, all by weight of the extract.

When an extract of avocado is mannoheptulose and then utilized in a composition herein, the mannoheptulose will be present from about 1% to about 99% of mannoheptulose, from about 5% to about 75% of the mannoheptulose, from about 10% to about 50% of the mannoheptulose, all by weight of the extract.

The dose of mannoheptulose used when obtained from a plant or avocado extract that is given to a mammal, on a daily basis, is from about 0.1 mg/kg to about 1000 mg/kg, from about 2 mg/kg to about 100 mg/kg, from about 2 mg/kg to about 5 mg/kg, wherein (as will be commonly understood in the art) the "mg" or "g" refers to level of the mannoheptulose and the "kg" refers to kilograms of the mammal or from about 0.001 gram to about 1 gram of mannoheptulose per kilogram of the mammal. When mannoheptulose obtained from a plant extract or avocado extract is present in a composition, the mannoheptulose is less than about 5%, or less than about 2%, or from about 0.0001% to about 0.5% of the mannoheptulose, all by weight of the composition. The level of mannoheptulose may be determined by one of ordinary skill in the art based on a variety of factors, for example, the form of the composition (e.g., whether a dry composition, moist composition, wet composition, or supplement, or any other form or mixture thereof). The ordinarily skilled artisan will be able to utilize the preferred optimal doses, and use these to determine the optimal level of component within a given composition.

The level of C-reactive protein in the blood subsequent to administration of a composition comprising an extract of mannoheptulose obtained from plant matter or avocado extract is from about 0 mg/L to about 100 mg/L, from about 0.1 mg/L to about 60 mg/L, from about 0.2 mg/L to about 40 mg/L, from about 0.3 mg/L to about 20 mg/L.

Compositions

It is anticipated that the glucose anti-metabolite or avocado or mannoheptulose or avocado extract described in the present invention can be added to any composition adapted for administration to a mammal.

Typical formulae for compositions are well known in the art. In addition to proteinaceous and farinaceous materials, the compositions of the invention generally may include vitamins, minerals, and other additives such as flavorings, preservatives, emulsifiers and humectants. The nutritional balance, including the relative proportions of vitamins, minerals, protein, fat and carbohydrate, is determined according to dietary standards known in the veterinary and nutritional art.

Nonlimiting examples of dry compositions may optionally contain on a dry matter basis, from about 1% to about 50% crude protein, from about 0.5% to about 25% crude fat, from about 1% to about 10% supplemental fiber, all by weight of the composition. The dry composition may have a total moisture content from about 1% to about 30% moisture. Alternatively, a dry composition may contain on a dry matter basis, from about 5% to about 35% crude protein, from about 5% to about 25% crude fat, from about 2% to about 8% supplemental fiber, all by weight of the composition. The dry composition may have a total moisture content from about 2% to about 20% moisture. Alternatively, the dry composition contains on a dry matter basis, a minimum protein level of about from about 9.5% to about 35%, a minimum fat level of from about 8% to about 20%, a minimum supplemental fiber level of from about 3% to about 7%, all by weight of the composition. The dry animal composition may also have a minimum metabolizable energy level of about 3.5 Kcal/g. The dry composition may have a total moisture content from about 3% to about 10%, Nonlimiting examples of a semi-moist composition may optionally contain on a dry matter basis, from about 0.5% to about 50% crude protein, from about 0.5% to about 25% crude fat, from about 0.5% to about 15% supplemental fiber, all by weight of the composition. The semi-moist composition may have a total moisture content from about 30% to about 50% moisture. Alternatively, the semi-moist compositions may contain on a dry matter basis, from about 5% to about 35% crude protein, from about 5% to about 25% crude fat, from about 1% to about 5% supplemental fiber, and all by weight of the composition. The semi-moist composition may have a total moisture content from about 35% to about 45% moisture. Alternatively, the semi-moist composition may have on a dry matter basis, a minimum protein level of about from about 9.5% to about 22%, a minimum fat level of from about 8% to about 13%, a minimum supplemental fiber level of from about 2% to about 3%, all by weight of the composition. The semi-moist composition may have a total moisture content from about 38% to about 42%. The semi-moist composition may also have a minimum metabolizable energy level of about 3.5 Kcal/g and from about 0.1% to about 20% ash, and from about 0.001% to about 5.0% taurine.

Nonlimiting examples of a moist composition may optionally contain on a dry matter basis, from about 0.5% to about 50% crude protein, from about 0.5% to about 25% crude fat, from about 0.01% to about 15% supplemental fiber, all by weight of the composition. The moist composition may have a total moisture content from about 50% to about 90% moisture. Alternatively, the moist compositions may contain on a dry matter basis, from about 5% to about 35% crude protein, from about 5% to about 25% crude fat, from about 0.05% to about 5% supplemental fiber, all by weight of the composition. The moist composition may have a total moisture content from about 60% to about 85% moisture. Alternatively, a moist animal composition may contain on a dry matter basis, a minimum protein level of about from about 9.5% to about 22%, a minimum fat level of from about 8% to about 13%, a minimum supplemental fiber level of from about 0.1% to about 3%, all by weight of the composition. The moist composition may have a total moisture content from about 65% to about 80%. The moist composition may also have a minimum metabolizable energy level of about 1.0 Kcal/g and from about 0.1% to about 20% ash, and from about 0.001% to about 5.0% taurine.

In one embodiment of the present invention, the composition is a composition, whether dry, moist, semi-moist or otherwise, that comprises on a dry matter basis, from about 5% to about 50%, alternatively 20% to about 50% of animal-derived ingredients, by weight of the composition. Non-limiting examples of animal-derived ingredients include chicken, beef, pork, lamb, turkey (or other animal) protein or fat, egg, fishmeal, and the like.

Where the composition is in the form of a gravy, the composition may comprise at least 10% of a broth, or stock, non-limiting examples of which include vegetable beef, chicken or ham stock. Typical gravy compositions may comprise on a dry matter basis, from about 0.5% to about 5% crude protein, and from about 2% to about 5% crude fat.

Where the composition is in the form of a supplement composition such as biscuits, chews, and other treats, the supplement may comprise, on a dry matter basis, from about 20% to about 60% protein, from about 22% to about 40% protein, by weight of the supplement composition. As another example, the supplement compositions may comprise, on a dry matter basis, from about 5% to about 35% fat, or from about 10% to about 30% fat, by weight of the supplement composition. Compositions and supplement compositions intended for use by animals such as cats or dogs are commonly known in the art.

Optional Ingredients

The composition of the present invention can further comprise a wide range of other optional ingredients.

Nonlimiting examples of additional components include animal protein, plant protein, farinaceous matter, vegetables, fruit, egg-based materials, undenatured proteins, food grade polymeric adhesives, gels, polyols, starches, gums, flavorants, seasonings, salts, colorants, time-release compounds, minerals, vitamins, antioxidants, prebiotics, probiotics, aroma modifiers, textured wheat protein, textured soy protein, textured lupin protein, textured vegetable protein, breading, comminuted meat, flour, comminuted pasta, water, and combinations thereof.

Nonlimiting examples of optional ingredients can include at least one vegetable. Nonlimiting examples of vegetables include carrots, peas, potatoes, cabbage, celery, beans, corn, tomatoes, broccoli, cauliflower, leeks and combinations thereof.

Also useful herein, as an optional ingredient, is a filler. The filler can be a solid, a liquid or packed air. The filler can be reversible (for example thermo-reversible including gelatin) and/or irreversible (for example thermo-irreversible including egg white). Nonlimiting examples of the filler include gravy, gel, jelly, aspic, sauce, water, air (for example including nitrogen, carbon dioxide, and atmospheric air), broth, and combinations thereof.

Nonlimiting examples of colorants include, but are not limited to, synthetic or natural colorants, and any combination thereof. When present the colorants are from about 0.0001% to about 5%, more from about 0.001% to about 1%, even more from about 0.005% to about 0.1%, on a dry matter basis, of said colorant.

Additionally, probiotic microorganisms, such as *Lactobacillus* or *Bifidobacterium* species, for example, may be added to the composition or the animal food compositions themselves.

Also useful herein, as an optional ingredient, is at least one fruit. Nonlimiting examples include tomatoes, apples, pears, peaches, cherries, apricots, plums, grapes, oranges, grapefruit, lemons, limes, cranberries, raspberries, blueberries, watermelon, cantelope, mushmellon, honeydew melon, strawberries, banana, and combinations thereof.

The composition may contain other active agents such as long chain fatty acids and zinc. Suitable long chain fatty acids include alpha-linoleic acid, gamma linolenic acid, linoleic acid, eicosapentanoic acid, and docosahexanoic acid. Fish oils are a suitable source of eicosapentanoic acids (EPA) and docosahexanoic acid (DHA). The DHA level is at least about 0.05%, alternatively at least about 0.1%, alternatively at least about 0.15% of the animal food composition, all on a dry matter basis. The EPA level is at least about 0.05%, alternatively at least about 0.1%, alternatively at least about 0.15% of the animal food composition, all on a dry matter basis.

The compositions of the present invention may further comprise a source of carbohydrate. Grains or cereals such as rice, corn, milo, sorghum, barley, wheat, and the like are illustrative sources.

The compositions may also contain other materials such as dried whey and other dairy by products.

Optional Processes for Preparing the Compositions of the Present Invention

The compositions may be prepared by any of a variety of processes including, but not limited to, optional processes described herein. Disclosed herein are optional processes for preparing the present inventive compositions. The ordinarily skilled artisan will understand, however, that the compositions are not limited by the following described processes.

A process for preparing the present compositions may comprise:
(a) providing plant matter;
(b) combining the plant matter with an aqueous solution and optionally with an enzyme, further optionally with heating, to provide a digested plant mixture;
(c) optionally separating any fractions present in the digested plant mixture, if any, to provide a carbohydrate extract;
(d) concentrating the digested plant mixture to enhance the concentration of carbohydrate therein; and
(e) combining the digested plant mixture with one or more composition components.

The plant matter may be any portion or whole of the plant, such as the leaves, fruit, seed or pit. In one optional process herein, the avocado is provided, and the process may commence with whole avocado fruit, including the pit or devoid (or partially devoid) of the pit. If the plant matter which is provided contains a pit, or partial pit, the pit or portion thereof may be optionally removed prior to further processing. Alfalfa, fig, or primrose may be similarly processed.

Additionally, in the production of a digested plant mixture can comprise combination of the plant matter with an aqueous solution, such as water, to assist with maceration of the plant into manageable constituents. Optionally but preferably, an enzyme having cellulose or pectin activity, or any combination thereof (such as a cellulase, hemicellulase, or pectinase) is included to assist with such maceration, including to assist with dissolution and release of carbohydrates via cell wall disruption. The utility of such an enzymatic treatment may be enhanced through heating during such maceration, such as from above ambient temperature to about 120° C., or to about 100° C., or from about 60° C. to about 120° C., or from about 60° C. to about 100° C. Agitation is further preferably utilized, typically for up to about 24 hours, but dependent upon the batch under processing. In one embodiment, the pH is controlled such to preserve enzyme activity, often in the range of pH from about 4 to about 6, preferably in the range of pH from about 5 to about 6. As such, depending upon such factors as ripeness of plant matter, quality of process aqueous solution (such as water added for process, for example), and the like, amounts of acid or base may be desirable as will be appreciated by one of ordinary skill in the art. Optionally, to assist with deactivation of the enzymes present, heating may be increased at the time of, or after, initial heating and agitation to form the digested plant mixture. Water is optionally heated to processing temperatures prior to the addition of the plant matter. Heat may be applied by a jacketed tank where low pressure steam is utilized. The digested plant mixture may result in fractions which may be separated in accordance with common techniques. For example, fractions present in the digested plant mixture may be separated by filtration to provide the carbohydrate extract as the resulting filtrate, with the filter cake being discarded. Other methods may include, but not be limited to, gravimetric, centrifugal, other filtrations, or combinations thereof.

The carbohydrate extract may then be concentrated, optionally utilizing at least one concentration method selected from the group consisting of heating, vacuum drying, evaporation, refractance window drying, freeze drying, spray drying, any other useful technique, or any combination of the foregoing. In one embodiment, at least one technique such as refractance window drying is used.

Once concentrated, the carbohydrate extract may be utilized in a composition of the present invention. In one embodiment herein, the present processes result in preferred yields of mannoheptulose or other components, based on the starting mass of the plant matter (e.g., avocado). In one embodiment, the yield of mannoheptulose present in the carbohydrate extract subsequent to concentration is less than about 20%, or from about 0.1% to about 10%, or from about 1% to about 7%, based on the starting mass of the plant matter. In another embodiment, the yield of the carbohydrate extract subsequent to concentration is less than about 30%, or from about 5% to about 25%, or from about 8% to about 20%, based on the starting mass of the plant matter. Of course, even higher yields may be desirable, and lower yields may also be acceptable.

C-Reactive Protein (CRP) Procedure

CRP analysis using Diasorin reagents (cat. No. 86083) has been adapted for use on the Hitachi 911 automated chemistry analyzer for samples. All samples are analyzed on the decreased sample size function of the Hitachi 911. Components of the Diasorin kit include polymer diluent, antibody reagent, and saline. CRP calibration standards and a human CRP control (cat. No. 86108) are used to generate a calibration curve and ensure the method is calibrated properly. The Diasorin CRP analysis is an immunopreciptin analysis. The sample and antiserum are mixed together forming insoluble complexes that produce turbidity and scatter light. The absorbance is then measured. Sample concentrations are interpolated from the calibration curve. Polymer diluent is used as is for T1 which dispenses 10 seconds after sample dispense. Antibody reagent diluted 1:7 with saline is used for T3 which dispenses 5 minutes after T1 is dispensed. The calibration type used is a full type using a blank (saline) and at least 3 programmed standards, 5 standards are used to ensure a broad range. The Diasorin kit comes with 5 standards, but we do not use the 100 standard (#5) and we dilute standard #2 1:10 with saline to increase our sensitivity range. Calibration type is Logit-Log 4P. The analysis uses a 2 point end (sample-blanked endpoint assay) with a primary wavelength of 340 nm and secondary wavelength of 700 nm. The CRP control and saline sample are analyzed with each run. After sample analysis has been completed a reaction monitor is viewed and printed for each sample. The reaction monitor allows a view in graph form of the photometric absorbance vs time. For CRPs cells are measured at 1-5, 6-10, 11-5, 16-20, 26-30, and 31-35. Cells 16-20 are compared with cells 31-35 and if cells 16-20 are higher than 31-35 a dilution must be performed (1:5 with saline) and the sample reanalyzed. Also all samples that read 0.0 upon initial analysis are diluted and reanalyzed to prevent false negative results, regardless of the cell comparisons. Results are reported in units of mg/L.

NOTE: Calibration standard values change periodically and should be put into the chemistry parameters of the Hitachi 911 when changed under the chemistry parameters menu.

Total Moisture Content Method

The method involves the analysis of the total moisture content in the composition. The analysis is based on the procedure outlined in AOAC method 930.15 and AACC method 44-19.

A composition sample is prepared by taking one unit volume, for example, 375 gram of the composition, and homogenizing in a food processor to a uniform consistency like a paste. A composition larger than 375 gram would be subdivided to create equal and representative fractions of the whole such that a 375 gram sample is obtained.

The paste of the composition is individually sampled in triplicate at a volume less than or equal to 100 ml and placed individually sealed in a 100 ml Nasco Whirl-Pak® (Fort Atkinson, Wis. 53538-0901). During the process of sealing the Whirl-Pak®, excess air is evacuated manually from the container just prior to final closure thereby minimizing the container headspace. The Whirl-Pak® is closed per manufacturer's instructions—tightly folding the bag over three (3) times and bending the tabs over 180 degrees.

All samples are refrigerated at 6° C. for less than 48 h prior to moisture analysis.

For total moisture analysis, the tare weight of each moisture tin and lid are recorded to 0.0001 g. Moisture tins and lids are handled using dry and clean forceps. Moisture tins and lids are held dry over desiccant in a sealed desiccator. A Whirl-Pak® containing a sample is unfolded and a 2.0000+/−0.2000 gram sample is weighed into the uncovered moisture tin. The weight of the sample in the moisture tin is recorded. The lid is placed atop the moisture tin in an open position to allow moisture loss but contain all other material during air oven drying. The lid and moisture tin loaded with sample are placed in an air oven operating at 135° C. for 6 h. Time is tracked using a count-down timer.

After drying, the tin is removed from the oven and the dried lid is placed atop the tin using forceps. The covered moisture tin with dried sample is placed immediately in a desiccator to cool. The sealed desiccator is filled below the stage with active desiccant. Once cool to room temperature, the covered moisture tin with dried sample is weighed to 0.0001 g and weight recorded. The total moisture content of each sample is calculated using the following formula:

Total Moisture Content(%)=100−(weight of tin, lid and sample after drying−empty tin and lid weight)×100 /initial sample weight.

EXAMPLES

The following examples further describe and demonstrate embodiments within the scope of the invention. The examples are given solely for the purpose of illustration and are not to be construed as limitations of the present invention, as many variations thereof are possible without departing from the spirit and scope of the invention. All of the following examples are compositions that are utilized by a mammal.

Examples 1-72

| Dry compositions | | | | | | |
|---|---|---|---|---|---|---|
| | Percentage % on dry matter basis (w/w) | | | | | |
| Ingredient | Example 1 | Example 2 | Example 3 | Example 4 | Example 5 | Example 6 |
| Protein products and meals | 26.4000 | 42.0000 | 45.3000 | 55.8000 | 56.0000 | 37.0000 |
| Cereal grains | 64.0500 | 43.0500 | 37.6500 | 27.4500 | 26.7500 | 45.9500 |
| Fat | 2.6000 | 5.8000 | 7.0000 | 6.0000 | 6.0000 | 7.0000 |
| Egg product | 3.5000 | 2.0000 | 3.0000 | 2.0000 | 2.0000 | 2.0000 |
| Vitamins | 0.2000 | 0.4000 | 0.6000 | 0.8000 | 0.4000 | 0.4000 |
| Minerals | 0.2000 | 0.8000 | 0.4000 | 0.8000 | 0.8000 | 0.6000 |
| Fiber | 3.0000 | 5.9000 | 6.0000 | 7.1000 | 8.0000 | 7.0000 |
| Avocado Extract | 0.0500 | 0.0500 | 0.0500 | 0.0500 | 0.0500 | 0.0500 |
| | Percentage % on dry matter basis (w/w) | | | | | |
| Ingredient | Example 7 | Example 8 | Example 9 | Example 10 | Example 11 | Example 12 |
| Protein products and meals | 26.4000 | 42.0000 | 45.3000 | 55.8000 | 56.0000 | 37.0000 |
| Cereal grains | 64.0975 | 43.0975 | 37.6975 | 27.4975 | 26.7975 | 45.9975 |
| Fat | 2.6000 | 5.8000 | 7.0000 | 6.0000 | 6.0000 | 7.0000 |
| Egg product | 3.5000 | 2.0000 | 3.0000 | 2.0000 | 2.0000 | 2.0000 |
| Vitamins | 0.2000 | 0.4000 | 0.6000 | 0.8000 | 0.4000 | 0.4000 |
| Minerals | 0.2000 | 0.8000 | 0.4000 | 0.8000 | 0.8000 | 0.6000 |
| Fiber | 3.0000 | 5.9000 | 6.0000 | 7.1000 | 8.0000 | 7.0000 |
| Avocado Extract | 0.0025 | 0.0025 | 0.0025 | 0.0025 | 0.0025 | 0.0025 |
| | Percentage % on dry matter basis (w/w) | | | | | |
| Ingredient | Example 13 | Example 14 | Example 15 | Example 16 | Example 17 | Example 18 |
| Protein products and meals | 21.4000 | 37.0000 | 40.2000 | 50.7000 | 51.0000 | 32.0000 |
| Cereal grains | 59.1000 | 38.1000 | 32.8000 | 22.6000 | 21.8000 | 41.0000 |
| Fat | 2.6000 | 5.8000 | 7.0000 | 6.0000 | 6.0000 | 7.0000 |
| Egg product | 3.5000 | 2.0000 | 3.0000 | 2.0000 | 2.0000 | 2.0000 |
| Vitamins | 0.2000 | 0.4000 | 0.6000 | 0.8000 | 0.4000 | 0.4000 |
| Minerals | 0.2000 | 0.8000 | 0.4000 | 0.8000 | 0.8000 | 0.6000 |
| Fiber | 3.0000 | 5.9000 | 6.0000 | 7.1000 | 8.0000 | 7.0000 |
| Avocado Extract | 10.0000 | 10.0000 | 10.0000 | 10.0000 | 10.0000 | 10.0000 |
| | Percentage % on dry matter basis (w/w) | | | | | |
| Ingredient | Example 19 | Example 20 | Example 21 | Example 22 | Example 23 | Example 24 |
| Protein products and meals | 25.9000 | 48.0000 | 45.0000 | 54.9000 | 56.0000 | 50.0000 |
| Cereal grains | 63.6000 | 36.1000 | 37.0000 | 27.4000 | 26.8000 | 32.0000 |
| Fat | 2.6000 | 5.8000 | 7.0000 | 6.0000 | 6.0000 | 7.0000 |
| Egg product | 3.5000 | 2.0000 | 3.0000 | 2.0000 | 2.0000 | 2.0000 |

-continued

| Dry compositions | | | | | | |
|---|---|---|---|---|---|---|
| Vitamins | 0.2000 | 0.4000 | 0.6000 | 0.8000 | 0.4000 | 0.4000 |
| Minerals | 0.2000 | 0.8000 | 0.4000 | 0.8000 | 0.8000 | 0.6000 |
| Fiber | 3.0000 | 5.9000 | 6.0000 | 7.1000 | 7.0000 | 7.0000 |
| Avocado | 1.0000 | 1.0000 | 1.0000 | 1.0000 | 1.0000 | 1.0000 |

| | Percentage % on dry matter basis (w/w) | | | | | |
|---|---|---|---|---|---|---|
| Ingredient | Example 25 | Example 26 | Example 27 | Example 28 | Example 29 | Example 30 |
| Protein products and meals | 25.9000 | 48.0000 | 45.0000 | 54.9000 | 56.0000 | 50.0000 |
| Cereal grains | 39.6000 | 12.1000 | 13.0000 | 3.4000 | 2.8000 | 8.0000 |
| Fat | 2.6000 | 5.8000 | 7.0000 | 6.0000 | 6.0000 | 7.0000 |
| Egg product | 3.5000 | 2.0000 | 3.0000 | 2.0000 | 2.0000 | 2.0000 |
| Vitamins | 0.2000 | 0.4000 | 0.6000 | 0.8000 | 0.4000 | 0.4000 |
| Minerals | 0.2000 | 0.8000 | 0.4000 | 0.8000 | 0.8000 | 0.6000 |
| Fiber | 3.0000 | 5.9000 | 6.0000 | 7.1000 | 7.0000 | 7.0000 |
| Avocado | 25.0000 | 25.0000 | 25.0000 | 25.0000 | 25.0000 | 25.0000 |

| | Percentage % on dry matter basis (w/w) | | | | | |
|---|---|---|---|---|---|---|
| Ingredient | Example 31 | Example 32 | Example 33 | Example 34 | Example 35 | Example 36 |
| Protein products and meals | 26.4000 | 48.5000 | 45.5000 | 55.4000 | 56.5000 | 50.5000 |
| Cereal grains | 64.0500 | 36.5500 | 37.4500 | 27.8500 | 27.2500 | 32.4500 |
| Fat | 2.6000 | 5.8000 | 7.0000 | 6.0000 | 6.0000 | 7.0000 |
| Egg product | 3.5000 | 2.0000 | 3.0000 | 2.0000 | 2.0000 | 2.0000 |
| Vitamins | 0.2000 | 0.4000 | 0.6000 | 0.8000 | 0.4000 | 0.4000 |
| Minerals | 0.2000 | 0.8000 | 0.4000 | 0.8000 | 0.8000 | 0.6000 |
| Fiber | 3.0000 | 5.9000 | 6.0000 | 7.1000 | 7.0000 | 7.0000 |
| Avocado | 0.0500 | 0.0500 | 0.0500 | 0.0500 | 0.0500 | 0.0500 |

| | Percentage % on dry matter basis (w/w) | | | | | |
|---|---|---|---|---|---|---|
| Ingredient | Example 37 | Example 38 | Example 39 | Example 40 | Example 41 | Example 42 |
| Protein products and meals | 26.4000 | 48.5000 | 45.0000 | 55.4000 | 56.5000 | 50.0000 |
| Cereal grains | 64.0800 | 36.5800 | 37.9800 | 27.8800 | 27.2800 | 32.9800 |
| Fat | 2.6000 | 5.8000 | 7.0000 | 6.0000 | 6.0000 | 7.0000 |
| Egg product | 3.5000 | 2.0000 | 3.0000 | 2.0000 | 2.0000 | 2.0000 |
| Vitamins | 0.2000 | 0.4000 | 0.6000 | 0.8000 | 0.4000 | 0.4000 |
| Minerals | 0.2000 | 0.8000 | 0.4000 | 0.8000 | 0.8000 | 0.6000 |
| Fiber | 3.0000 | 5.9000 | 6.0000 | 7.1000 | 7.0000 | 7.0000 |
| Mannoheptulose | 0.0200 | 0.0200 | 0.0200 | 0.0200 | 0.0200 | 0.0200 |

| | Percentage % on dry matter basis (w/w) | | | | | |
|---|---|---|---|---|---|---|
| Ingredient | Example 43 | Example 44 | Example 45 | Example 46 | Example 47 | Example 48 |
| Protein products and meals | 26.4000 | 48.4000 | 45.0000 | 55.4000 | 56.5000 | 50.0000 |
| Cereal grains | 64.0990 | 36.6990 | 37.9990 | 27.8990 | 27.2990 | 32.9990 |
| Fat | 2.6000 | 5.8000 | 7.0000 | 6.0000 | 6.0000 | 7.0000 |
| Egg product | 3.5000 | 2.0000 | 3.0000 | 2.0000 | 2.0000 | 2.0000 |
| Vitamins | 0.2000 | 0.4000 | 0.6000 | 0.8000 | 0.4000 | 0.4000 |
| Minerals | 0.2000 | 0.8000 | 0.4000 | 0.8000 | 0.8000 | 0.6000 |
| Fiber | 3.0000 | 5.9000 | 6.0000 | 7.1000 | 7.0000 | 7.0000 |
| Mannoheptulose | 0.0010 | 0.0010 | 0.0010 | 0.0010 | 0.0010 | 0.0010 |

| | Percentage % on dry matter basis (w/w) | | | | | |
|---|---|---|---|---|---|---|
| Ingredient | Example 49 | Example 50 | Example 51 | Example 52 | Example 53 | Example 54 |
| Protein products and meals | 21.4000 | 43.4000 | 40.0000 | 50.4000 | 51.5000 | 45.0000 |
| Cereal grains | 59.1000 | 31.7000 | 33.0000 | 22.9000 | 22.3000 | 28.0000 |
| Fat | 2.6000 | 5.8000 | 7.0000 | 6.0000 | 6.0000 | 7.0000 |
| Egg product | 3.5000 | 2.0000 | 3.0000 | 2.0000 | 2.0000 | 2.0000 |
| Vitamins | 0.2000 | 0.4000 | 0.6000 | 0.8000 | 0.4000 | 0.4000 |
| Minerals | 0.2000 | 0.8000 | 0.4000 | 0.8000 | 0.8000 | 0.6000 |
| Fiber | 3.0000 | 5.9000 | 6.0000 | 7.1000 | 7.0000 | 7.0000 |
| Mannoheptulose | 10.0000 | 10.0000 | 10.0000 | 10.0000 | 10.0000 | 10.0000 |

| | Percentage % on dry matter basis (w/w) | | | | | |
|---|---|---|---|---|---|---|
| Ingredient | Example 55 | Example 56 | Example 57 | Example 58 | Example 59 | Example 60 |
| Protein products and meals | 26.4000 | 48.4000 | 45.0000 | 55.4000 | 56.5000 | 50.0000 |
| Cereal grains | 64.0800 | 36.6800 | 37.9800 | 27.8800 | 27.2800 | 32.9800 |
| Fat | 2.6000 | 5.8000 | 7.0000 | 6.0000 | 6.0000 | 7.0000 |

-continued

| Dry compositions | | | | | | |
|---|---|---|---|---|---|---|
| Egg product | 3.5000 | 2.0000 | 3.0000 | 2.0000 | 2.0000 | 2.0000 |
| Vitamins | 0.2000 | 0.4000 | 0.6000 | 0.8000 | 0.4000 | 0.4000 |
| Minerals | 0.2000 | 0.8000 | 0.4000 | 0.8000 | 0.8000 | 0.6000 |
| Fiber | 3.0000 | 5.9000 | 6.0000 | 7.1000 | 7.0000 | 7.0000 |
| Glucose Anti-Metabolite | 0.0200 | 0.0200 | 0.0200 | 0.0200 | 0.0200 | 0.0200 |

| | Percentage % on dry matter basis (w/w) | | | | | |
|---|---|---|---|---|---|---|
| Ingredient | Example 61 | Example 62 | Example 63 | Example 64 | Example 65 | Example 66 |
| Protein products and meals | 26.4000 | 48.4000 | 45.0000 | 55.4000 | 56.5000 | 50.0000 |
| Cereal grains | 64.0990 | 36.6990 | 37.9990 | 27.8990 | 27.2990 | 32.9990 |
| Fat | 2.6000 | 5.8000 | 7.0000 | 6.0000 | 6.0000 | 7.0000 |
| Egg product | 3.5000 | 2.0000 | 3.0000 | 2.0000 | 2.0000 | 2.0000 |
| Vitamins | 0.2000 | 0.4000 | 0.6000 | 0.8000 | 0.4000 | 0.4000 |
| Minerals | 0.2000 | 0.8000 | 0.4000 | 0.8000 | 0.8000 | 0.6000 |
| Fiber | 3.0000 | 5.9000 | 6.0000 | 7.1000 | 7.0000 | 7.0000 |
| Glucose Anti-Metabolite | 0.0010 | 0.0010 | 0.0010 | 0.0010 | 0.0010 | 0.0010 |

| | Percentage % on dry matter basis (w/w) | | | | | |
|---|---|---|---|---|---|---|
| Ingredient | Example 67 | Example 68 | Example 69 | Example 70 | Example 71 | Example 72 |
| Protein products and meals | 21.4000 | 43.5000 | 40.0000 | 50.4000 | 51.5000 | 45.0000 |
| Cereal grains | 59.1000 | 31.6000 | 33.0000 | 22.9000 | 22.3000 | 28.0000 |
| Fat | 2.6000 | 5.8000 | 7.0000 | 6.0000 | 6.0000 | 7.0000 |
| Egg product | 3.5000 | 2.0000 | 3.0000 | 2.0000 | 2.0000 | 2.0000 |
| Vitamins | 0.2000 | 0.4000 | 0.6000 | 0.8000 | 0.4000 | 0.4000 |
| Minerals | 0.2000 | 0.8000 | 0.4000 | 0.8000 | 0.8000 | 0.6000 |
| Fiber | 3.0000 | 5.9000 | 6.0000 | 7.1000 | 7.0000 | 7.0000 |
| Glucose Anti-Metabolite | 10.0000 | 10.0000 | 10.0000 | 10.0000 | 10.0000 | 10.0000 |

The dry compositions of Examples 1-72 can be made by first, milling and mixing the cereal grains with protein meal, egg products, vitamins and minerals and fiber sources and avocado or avocado extract or mannoheptulose or glucose anti-metabolite. Then, add the mixed, dried ingredients to the meat products and fat sources. Extrude the ingredients into kibbles. Dry the kibbles. Package the finished product.

Examples 73-144

| Wet compositions | | | | | | |
|---|---|---|---|---|---|---|
| | Percentage % on matter basis (w/w) | | | | | |
| Ingredient | Example 73 | Example 74 | Example 75 | Example 76 | Example 77 | Example 78 |
| Protein products and meal | 82.7000 | 44.9000 | 54.0000 | 65.3000 | 63.4000 | 48.4000 |
| Cereal grains | 11.4000 | 43.7000 | 35.9000 | 29.9000 | 30.1000 | 45.7000 |
| Fat | 0.0000 | 2.0000 | 1.0000 | 1.0000 | 1.0000 | 2.0000 |
| Egg product | 2.5000 | 2.0000 | 3.0000 | 2.0000 | 2.0000 | 3.4000 |
| Vitamins | 0.1000 | 0.4000 | 0.6000 | 0.8000 | 0.4000 | 0.1000 |
| Minerals | 0.1000 | 0.8000 | 0.4000 | 0.8000 | 0.4000 | 0.2000 |
| Fiber | 3.0000 | 6.0000 | 4.9000 | 0.0000 | 2.5000 | 0.0000 |
| Avocado Extract | 0.2000 | 0.2000 | 0.2000 | 0.2000 | 0.2000 | 0.2000 |

| | Percentage % on dry matter basis (w/w) | | | | | |
|---|---|---|---|---|---|---|
| Ingredient | Example 79 | Example 80 | Example 81 | Example 82 | Example 83 | Example 84 |
| Protein products and meal | 82.7000 | 44.9000 | 54.0000 | 65.4000 | 63.5000 | 48.4000 |
| Cereal grains | 11.5900 | 43.8900 | 36.0900 | 29.9900 | 30.1900 | 45.8900 |
| Fat | 0.0000 | 2.0000 | 1.0000 | 1.0000 | 1.0000 | 2.0000 |
| Egg product | 2.5000 | 2.0000 | 3.0000 | 2.0000 | 2.0000 | 3.4000 |
| Vitamins | 0.1000 | 0.4000 | 0.6000 | 0.8000 | 0.4000 | 0.1000 |
| Minerals | 0.1000 | 0.8000 | 0.4000 | 0.8000 | 0.4000 | 0.2000 |
| Fiber | 3.0000 | 6.0000 | 4.9000 | 0.0000 | 2.5000 | 0.0000 |
| Avocado Extract | 0.0100 | 0.0100 | 0.0100 | 0.0100 | 0.0100 | 0.0100 |

| | Percentage % on dry matter basis (w/w) | | | | | |
|---|---|---|---|---|---|---|
| Ingredient | Example 85 | Example 86 | Example 87 | Example 88 | Example 89 | Example 90 |
| Protein products and meal | 72.7000 | 35.0000 | 44.1000 | 55.4000 | 53.5000 | 38.5000 |
| Cereal grains | 1.6000 | 33.8000 | 25.0000 | 20.0000 | 20.2000 | 35.8000 |
| Fat | 0.0000 | 2.0000 | 2.0000 | 1.0000 | 1.0000 | 2.0000 |

-continued

| | | | Wet compositions | | | |
|---|---|---|---|---|---|---|
| Egg product | 2.5000 | 2.0000 | 3.0000 | 2.0000 | 2.0000 | 3.4000 |
| Vitamins | 0.1000 | 0.4000 | 0.6000 | 0.8000 | 0.4000 | 0.1000 |
| Minerals | 0.1000 | 0.8000 | 0.4000 | 0.8000 | 0.4000 | 0.2000 |
| Fiber | 3.0000 | 6.0000 | 4.9000 | 0.0000 | 2.5000 | 0.0000 |
| Avocado Extract | 20.0000 | 20.0000 | 20.0000 | 20.0000 | 20.0000 | 20.0000 |

| | Percentage % on dry matter basis (w/w) | | | | | |
|---|---|---|---|---|---|---|
| Ingredient | Example 91 | Example 92 | Example 93 | Example 94 | Example 95 | Example 96 |
| Protein products and meal | 80.7000 | 43.0000 | 52.1000 | 63.4000 | 61.5000 | 46.5000 |
| Cereal grains | 9.6000 | 41.8000 | 34.0000 | 28.0000 | 28.2000 | 43.8000 |
| Fat | 0.0000 | 2.0000 | 1.0000 | 1.0000 | 1.0000 | 2.0000 |
| Egg product | 2.5000 | 2.0000 | 3.0000 | 2.0000 | 2.0000 | 3.4000 |
| Vitamins | 0.1000 | 0.4000 | 0.6000 | 0.8000 | 0.4000 | 0.1000 |
| Minerals | 0.1000 | 0.8000 | 0.4000 | 0.8000 | 0.4000 | 0.2000 |
| Fiber | 3.0000 | 6.0000 | 4.9000 | 0.0000 | 2.5000 | 0.0000 |
| Avocado | 4.0000 | 4.0000 | 4.0000 | 4.0000 | 4.0000 | 4.0000 |

| | Percentage % on dry matter basis (w/w) | | | | | |
|---|---|---|---|---|---|---|
| Ingredient | Example 97 | Example 98 | Example 99 | Example 100 | Example 101 | Example 102 |
| Protein products and meal | 82.6000 | 44.9000 | 54.0000 | 65.3000 | 63.4000 | 48.4000 |
| Cereal grains | 11.5000 | 43.7000 | 35.9000 | 29.9000 | 30.1000 | 45.7000 |
| Fat | 0.0000 | 2.0000 | 1.0000 | 1.0000 | 1.0000 | 2.0000 |
| Egg product | 2.5000 | 2.0000 | 3.0000 | 2.0000 | 2.0000 | 3.4000 |
| Vitamins | 0.1000 | 0.4000 | 0.6000 | 0.8000 | 0.4000 | 0.1000 |
| Minerals | 0.1000 | 0.8000 | 0.4000 | 0.8000 | 0.4000 | 0.2000 |
| Fiber | 3.0000 | 6.0000 | 4.9000 | 0.0000 | 2.5000 | 0.0000 |
| Avocado | 0.2000 | 0.2000 | 0.2000 | 0.2000 | 0.2000 | 0.2000 |

| | Percentage % on dry matter basis (w/w) | | | | | |
|---|---|---|---|---|---|---|
| Ingredient | Example 103 | Example 104 | Example 105 | Example 106 | Example 107 | Example 108 |
| Protein products and meal | 72.7000 | 35.0000 | 44.1000 | 55.4000 | 53.5000 | 38.5000 |
| Cereal grains | 1.6000 | 33.8000 | 26.0000 | 20.0000 | 20.2000 | 35.8000 |
| Fat | 0.0000 | 2.0000 | 1.0000 | 1.0000 | 1.0000 | 2.0000 |
| Egg product | 2.5000 | 2.0000 | 3.0000 | 2.0000 | 2.0000 | 3.4000 |
| Vitamins | 0.1000 | 0.4000 | 0.6000 | 0.8000 | 0.4000 | 0.1000 |
| Minerals | 0.1000 | 0.8000 | 0.4000 | 0.8000 | 0.4000 | 0.2000 |
| Fiber | 3.0000 | 6.0000 | 4.9000 | 0.0000 | 2.5000 | 0.0000 |
| Avocado | 20.0000 | 20.0000 | 20.0000 | 20.0000 | 20.0000 | 20.0000 |

| | Percentage % on dry matter basis (w/w) | | | | | |
|---|---|---|---|---|---|---|
| Ingredient | Example 109 | Example 110 | Example 111 | Example 112 | Example 113 | Example 114 |
| Protein products and meal | 82.7000 | 44.9000 | 54.0000 | 65.3000 | 63.4000 | 48.3000 |
| Cereal grains | 11.5200 | 43.8200 | 35.0200 | 30.0200 | 30.2000 | 45.9200 |
| Fat | 0.0000 | 2.0000 | 2.0000 | 1.0000 | 1.0000 | 2.0000 |
| Egg product | 2.5000 | 2.0000 | 3.0000 | 2.0000 | 2.0000 | 3.4000 |
| Vitamins | 0.1000 | 0.4000 | 0.6000 | 0.8000 | 0.4000 | 0.1000 |
| Minerals | 0.1000 | 0.8000 | 0.4000 | 0.8000 | 0.4000 | 0.2000 |
| Fiber | 3.0000 | 6.0000 | 4.9000 | 0.0000 | 2.5000 | 0.0000 |
| Mannoheptulose | 0.0800 | 0.0800 | 0.0800 | 0.0800 | 0.0800 | 0.0800 |

| | Percentage % on dry matter basis (w/w) | | | | | |
|---|---|---|---|---|---|---|
| Ingredient | Example 115 | Example 116 | Example 117 | Example 118 | Example 119 | Example 120 |
| Protein products and meal | 82.7000 | 44.9000 | 54.0000 | 65.4000 | 63.5000 | 48.4000 |
| Cereal grains | 11.5960 | 43.8960 | 36.0960 | 29.9960 | 30.1960 | 45.8960 |
| Fat | 0.0000 | 2.0000 | 1.0000 | 1.0000 | 1.0000 | 2.0000 |
| Egg product | 2.5000 | 2.0000 | 3.0000 | 2.0000 | 2.0000 | 3.4000 |
| Vitamins | 0.1000 | 0.4000 | 0.6000 | 0.8000 | 0.4000 | 0.1000 |
| Minerals | 0.1000 | 0.8000 | 0.4000 | 0.8000 | 0.4000 | 0.2000 |
| Fiber | 3.0000 | 6.0000 | 4.9000 | 0.0000 | 2.5000 | 0.0000 |
| Mannoheptulose | 0.0040 | 0.0040 | 0.0040 | 0.0040 | 0.0040 | 0.0040 |

-continued

Wet compositions

Percentage % on dry matter basis (w/w)

| Ingredient | Example 121 | Example 122 | Example 123 | Example 124 | Example 125 | Example 126 |
|---|---|---|---|---|---|---|
| Protein products and meal | 77.7000 | 40.0000 | 49.1000 | 60.4000 | 58.5000 | 43.5000 |
| Cereal grains | 6.6000 | 38.8000 | 31.0000 | 25.0000 | 25.2000 | 40.8000 |
| Fat | 0.0000 | 2.0000 | 1.0000 | 1.0000 | 1.0000 | 2.0000 |
| Egg product | 2.5000 | 2.0000 | 3.0000 | 2.0000 | 2.0000 | 3.4000 |
| Vitamins | 0.1000 | 0.4000 | 0.6000 | 0.8000 | 0.4000 | 0.1000 |
| Minerals | 0.1000 | 0.8000 | 0.4000 | 0.8000 | 0.4000 | 0.2000 |
| Fiber | 3.0000 | 6.0000 | 4.9000 | 0.0000 | 2.5000 | 0.0000 |
| Mannoheptulose | 10.0000 | 10.0000 | 10.0000 | 10.0000 | 10.0000 | 10.0000 |

Percentage % on dry matter basis (w/w)

| Ingredient | Example 127 | Example 128 | Example 129 | Example 130 | Example 131 | Example 132 |
|---|---|---|---|---|---|---|
| Protein products and meal | 82.7000 | 44.9000 | 54.0000 | 65.3000 | 63.4000 | 48.3000 |
| Cereal grains | 11.5200 | 43.8200 | 35.0200 | 30.0200 | 30.2200 | 45.9200 |
| Fat | 0.0000 | 2.0000 | 2.0000 | 1.0000 | 1.0000 | 2.0000 |
| Egg product | 2.5000 | 2.0000 | 3.0000 | 2.0000 | 2.0000 | 3.4000 |
| Vitamins | 0.1000 | 0.4000 | 0.6000 | 0.8000 | 0.4000 | 0.1000 |
| Minerals | 0.1000 | 0.8000 | 0.4000 | 0.8000 | 0.4000 | 0.2000 |
| Fiber | 3.0000 | 6.0000 | 4.9000 | 0.0000 | 2.5000 | 0.0000 |
| Glucose Anti-Metabolite | 0.0800 | 0.0800 | 0.0800 | 0.0800 | 0.0800 | 0.0800 |

Percentage % on dry matter basis (w/w)

| Ingredient | Example 133 | Example 134 | Example 135 | Exampl3 136 | Example 137 | Example 138 |
|---|---|---|---|---|---|---|
| Protein products and meal | 82.7000 | 44.9000 | 54.0000 | 65.4000 | 63.5000 | 48.4000 |
| Cereal grains | 11.5960 | 43.8960 | 36.0960 | 29.9960 | 30.1960 | 45.8960 |
| Fat | 0.0000 | 2.0000 | 1.0000 | 1.0000 | 1.0000 | 2.0000 |
| Egg product | 2.5000 | 2.0000 | 3.0000 | 2.0000 | 2.0000 | 3.4000 |
| Vitamins | 0.1000 | 0.4000 | 0.6000 | 0.8000 | 0.4000 | 0.1000 |
| Minerals | 0.1000 | 0.8000 | 0.4000 | 0.8000 | 0.4000 | 0.2000 |
| Fiber | 3.0000 | 6.0000 | 4.9000 | 0.0000 | 2.5000 | 0.0000 |
| Glucose Anti-Metabolite | 0.0040 | 0.0040 | 0.0040 | 0.0040 | 0.0040 | 0.0040 |

Percentage % on dry matter basis (w/w)

| Ingredient | Example 139 | Example 140 | Example 141 | Example 142 | Example 143 | Example 144 |
|---|---|---|---|---|---|---|
| Protein products and meal | 77.7000 | 40.0000 | 49.1000 | 60.4000 | 58.5000 | 43.5000 |
| Cereal grains | 6.6000 | 38.8000 | 30.0000 | 25.0000 | 25.2000 | 40.8000 |
| Fat | 0.0000 | 2.0000 | 2.0000 | 1.0000 | 1.0000 | 2.0000 |
| Egg product | 2.5000 | 2.0000 | 3.0000 | 2.0000 | 2.0000 | 3.4000 |
| Vitamins | 0.1000 | 0.4000 | 0.6000 | 0.8000 | 0.4000 | 0.1000 |
| Minerals | 0.1000 | 0.8000 | 0.4000 | 0.8000 | 0.4000 | 0.2000 |
| Fiber | 3.0000 | 6.0000 | 4.9000 | 0.0000 | 2.5000 | 0.0000 |
| Glucose Anti-Metabolite | 10.0000 | 10.0000 | 10.0000 | 10.0000 | 10.0000 | 10.0000 |

The wet compositions of Examples 73-144 can be made by first drying and milling cereal grains. Mix dried cereal grains, Protein meals, egg product, vitamins, minerals and fiber sources and avocado or avocado extract or mannoheptulose or glucose anti-metabolite. Blend dry ingredients with meat products and fat sources. The mixture is packaged into cans and cooked via retort process to provided finished product. For preformed pieces (chunks in gravy) mixture is extruded, passed through a steam tunnel for preconditioning, cut to desired shape, packaged with added water and retorted to provide safe finished product.

It should be understood that every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressly written herein.

All parts, ratios, and percentages herein, in the Specification, Examples, and Claims, are by weight and all numerical limits are used with the normal degree of accuracy afforded by the art, unless otherwise specified.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed:

1. A method for decreasing inflammation and stress in a mammal comprising: administration to a mammal a composition comprising avocado fruit; and wherein said composition comprises amounts of the avocado fruit sufficient to lower a level of a C-reactive protein in the blood of the mammal subsequent to administration of the avocado;

wherein administration is daily and the dose of avocado fruit is about 100 mg/kg to about 200 g/kg; and wherein the composition comprises less than 5% of said avocado fruit, by weight of the composition.

2. The method of claim 1, wherein the level of said C-reactive protein in the blood subsequent to administration of the avocado is from about 0 mg/L to about 100 mg/L.

3. The method of claim 1, wherein the administration is oral.

4. The method of claim 1, wherein said composition is selected from the group consisting of pet food, dog food, cat food, treats, chew, biscuits, gravy, sauce, beverage, supplemental water, and combinations thereof.

5. The method of claim 4, wherein the composition is a nutritionally balanced pet food composition.

6. The method of claim 1, further comprising animal protein, plant protein, farinaceous matter, vegetables, fruit, egg-based materials, undenatured proteins, food grade polymeric adhesives, gels, polyols, starches, gums, flavorants, seasonings, salts, colorants, time-release compounds, minerals, vitamins, antioxidants, prebiotics, probiotics, aroma modifiers, lipids, and combinations thereof.

7. The method of claim 1, wherein the level of said C-reactive protein in the blood subsequent to administration of the avocado is from about 0 mg/L to about 100 mg/L.

8. A method for decreasing inflammation and stress in a mammal comprising: administration to a mammal a composition comprising mannoheptulose; and wherein said composition comprises amounts of the mannoheptulose sufficient to lower the level of a C-reactive protein in the blood of the mammal subsequent to administration of the mannoheptulose;

wherein administration is daily and the dose of mannoheptulose is about 2 mg/kg to about 5 mg/kg; and wherein the composition comprises less than 5% of said mannoheptulose, by weight of the composition.

9. The method of claim 8, wherein the level of said C-reactive protein in the blood subsequent to administration of the mannoheptulose is from about 0 mg/L to about 100 mg/L.

10. The method of claim 8, wherein the level of said C-reactive protein in the blood subsequent to administration of the mannoheptulose is from about 0.1 mg/L to about 60 mg/L.

11. The method of claim 8, wherein the level of said C-reactive protein in the blood subsequent to administration of the mannoheptulose is from about 0.2 mg/L to about 40 mg/L.

12. The method of claim 8, wherein said mannoheptulose is selected from the group consisting of avocado extract, avocado, and combinations thereof.

13. The method of claim 8, wherein the administration is oral.

14. The method of claim 8, wherein said composition is selected from the group consisting of pet food, dog food, cat food, treats, chew, biscuits, gravy, sauce, beverage, supplemental water, and combinations thereof.

15. The method of claim 8, wherein the composition is a nutritionally balanced pet food composition.

16. The method of claim 8, further comprising animal protein, plant protein, farinaceous matter, vegetables, fruit, egg-based materials, undenatured proteins, food grade polymeric adhesives, gels, polyols, starches, gums, flavorants, seasonings, salts, colorants, time-release compounds, minerals, vitamins, antioxidants, prebiotics, probiotics, aroma modifiers, lipids, and combinations thereof.

17. A method for decreasing inflammation and stress in a mammal comprising: administration to a mammal a composition comprising avocado extract; and wherein said composition comprises amounts of the avocado extract sufficient to lower the level of a C-reactive protein in the blood of the mammal subsequent to administration of the avocado extract;

wherein administration is daily and the avocado extract comprises a dose of glucose anti-metabolite at about 2 mg/kg to about 5 mg/kg; and wherein the composition comprises less than 5% of said avocado extract, by weight of the composition.

18. The method of claim 17, wherein the level of said C-reactive protein in the blood subsequent to administration of the avocado extract is from about 0 mg/L to about 100 mg/L.

19. The method of claim 17, wherein the level of said C-reactive protein in the blood subsequent to administration of the avocado extract is from about 0.1 mg/L to about 60 mg/L.

20. The method of claim 17, wherein the level of said C-reactive protein in the blood subsequent to administration of the avocado extract is from about 0.2 mg/L to about 40 mg/L.

21. The method of claim 17, wherein the administration is oral.

22. The method of claim 17, wherein said composition is selected from the group consisting of pet food, dog food, cat food, treats, chew, biscuits, gravy, sauce, beverage, supplemental water, and combinations thereof.

23. The method of claim 17, wherein the composition is a nutritionally balanced pet food composition.

24. The method of claim 17 further comprising animal protein, plant protein, farinaceous matter, vegetables, fruit, egg-based materials, undenatured proteins, food grade polymeric adhesives, gels, polyols, starches, gums, flavorants, seasonings, salts, colorants, time-release compounds, minerals, vitamins, antioxidants, prebiotics, probiotics, aroma modifiers, lipids, and combinations thereof.

* * * * *